United States Patent [19]
Bonhomme et al.

[11] Patent Number: 5,789,566
[45] Date of Patent: Aug. 4, 1998

[54] DNA SEQUENCE IMPARTING CYTOPLASMIC MALE STERILITY, MITOCHONDRIAL GENOME, NUCLEAR GENOME, MITOCHONDRIA AND PLANT CONTAINING SAID SEQUENCE AND PROCESS FOR THE PREPARATION OF HYBRIDS

[75] Inventors: Sandrine Bonhomme, Paris; Françoise Budar, Limours; Dominique Lancelin, Buc; Georges Pelletier, Bures/Yvette, all of France

[73] Assignee: Institut National de la Recherche Agronomique, Paris, France

[21] Appl. No.: 490,099

[22] Filed: Jun. 6, 1995

Related U.S. Application Data

[63] Continuation of Ser. No. 30,083, filed as PCT/FR91/00741 Sep. 20, 1991, published as WO92/05251 Apr. 2, 1992, abandoned.

[30] Foreign Application Priority Data

Sep. 21, 1990 [FR] France .................................. 90 11670

[51] Int. Cl.$^6$ .................................. C12N 15/00
[52] U.S. Cl. .................. 536/23.6; 800/DIG. 15; 800/255; 435/317.1; 435/410; 435/419
[58] Field of Search ..................... 800/DIG. 15, 16, 800/17, 255; 536/23.6, 24.32, 24.31; 435/240.4, 317.1, 410, 419

[56] References Cited

PUBLICATIONS

Pelletier et al. Molec. Gen. Genet. 191: 244–250 (1983).
Chetrit et al. Theor. Appl. Genet. 69: 361–366 (1985).
Vedel et al. Plant Physiol. Biochem 25: 249–257 (1987).
Makaroff et al. Jour. Biological Chem. 264: 11706–11713 (1989).
Bonhomme et al. Curr. Genet. 19: 121–127 (1991).
Makaroff Sequence Alligment with SEQ ID No: 1 (3 pages).
Reeck et al., Cell 50: 667, Aug. 28, 1987.
Lewin. Science 237: 1570, 1987.
Turpen et al., Mol. Gen. Genet. 209(2):227–233, 1987.

*Primary Examiner*—Scott W. Houtteman
*Attorney, Agent, or Firm*—Cooley Godward LLP

[57] ABSTRACT

Ogura sterility DNA is used to develop agronomically valuable hybrids that lack the undesirable features of plants having Ogura DNA (chlorosis at low temperature; poor fertile fertility; aberrant flower morphology) but still impart efficient male sterility (which can be easily restored). Ogura sterility is carried by a DNA sequence defined by nucleotides 928-2273 of a 2428 base sequence reproduced in the specification. When present in mitochondrial or nuclear genome of a plant it confers cytoplasmic male sterility. Also disclosed are recombinant plant nuclear and mitochondrial genomes containing a DNA sequence defined by nucleotides 928-1569 of the specified sequence (or its homologous); cytoplasm containing such a mitochondrial genome; Brassica plants or hybrids containing the sterility DNA; and, DNA probes of at least 10 bases from the 928-1569 sequences. DNA probes are used to detect male sterility and for selecting clones without the need for lengthy agronomic/rehybridization steps.

28 Claims, 22 Drawing Sheets

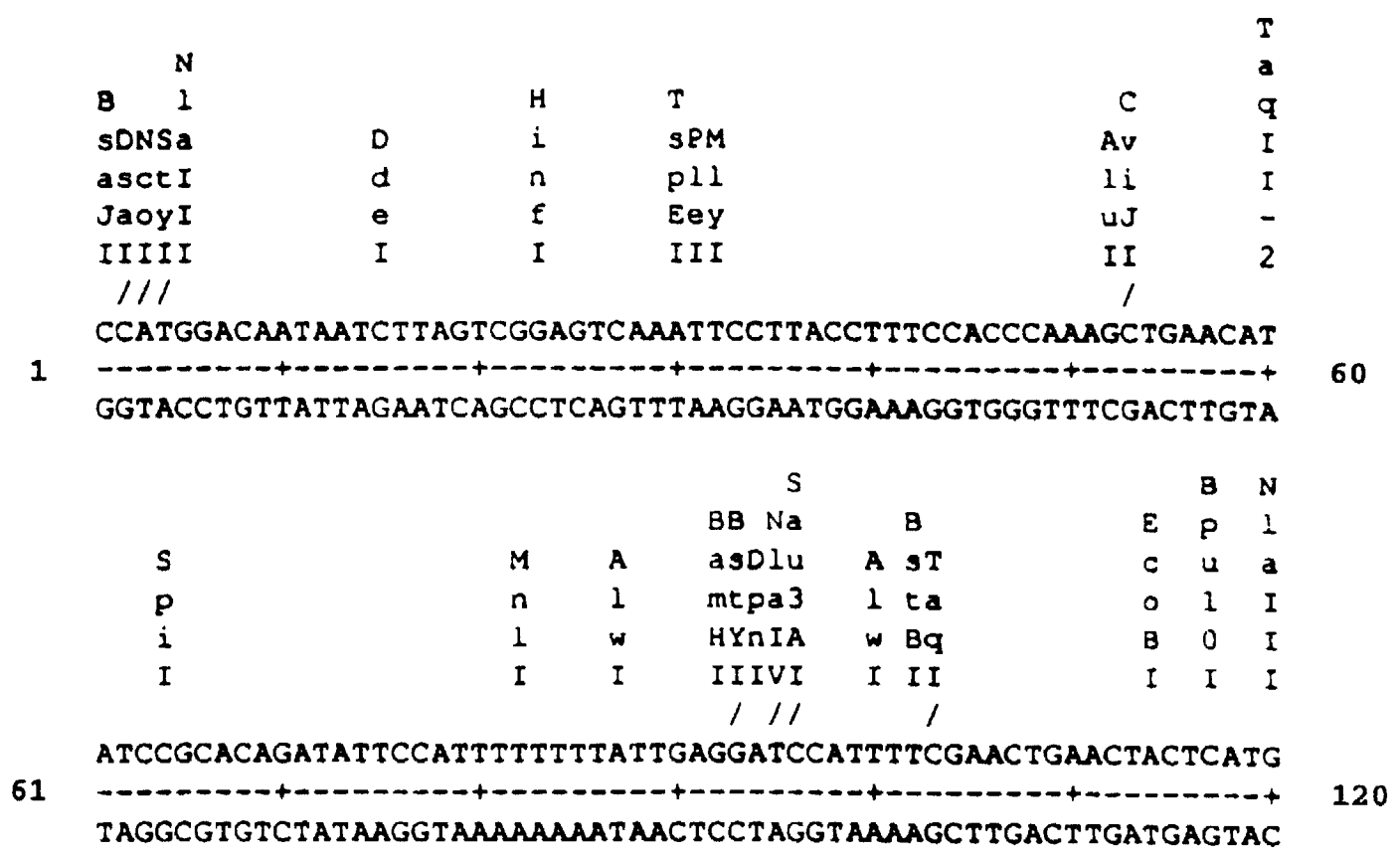

FIG._1A

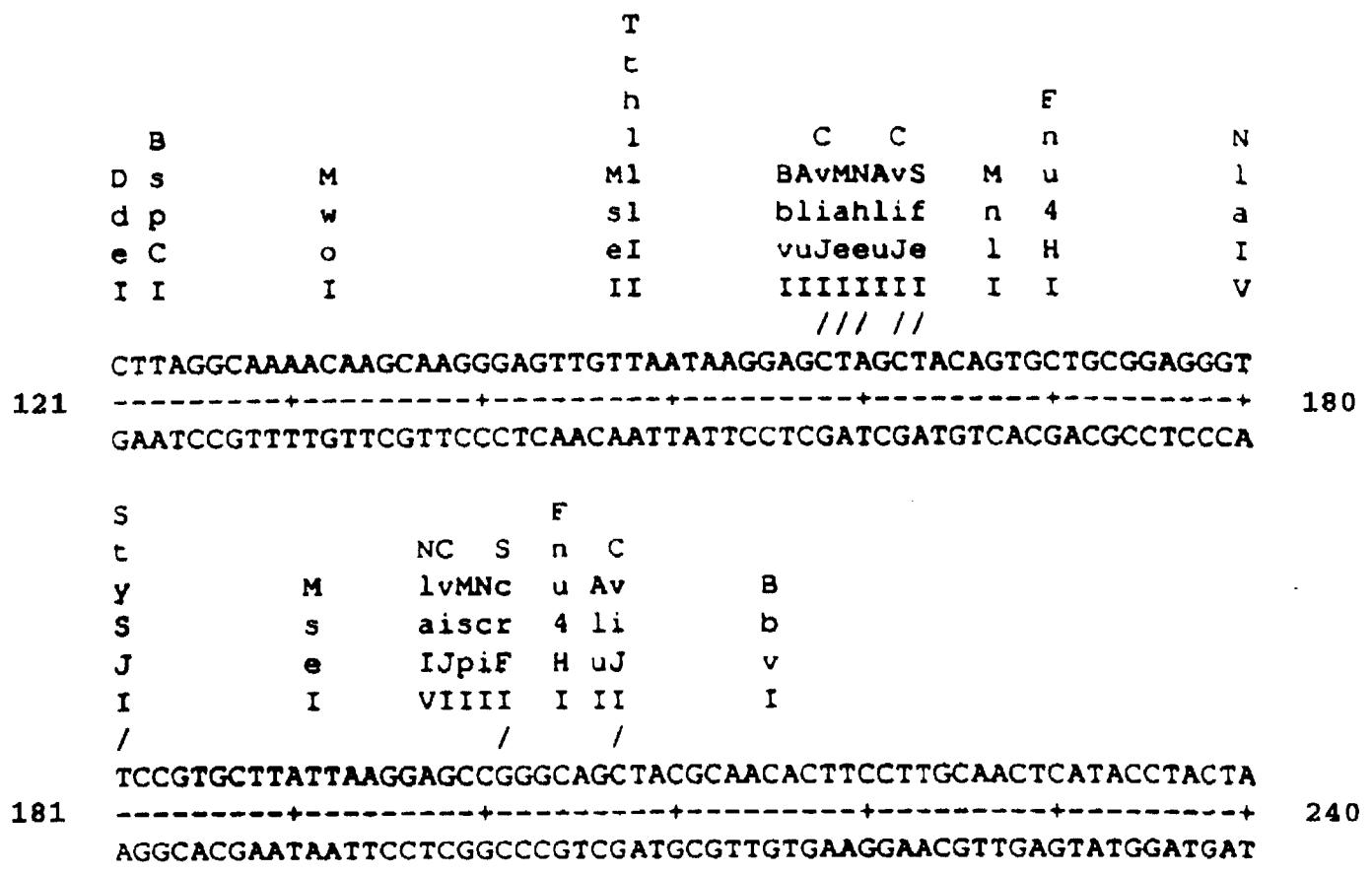

FIG._1B

```
                                              E
                                              Cn              E  E
                                              AvuBF    M      c  o       MBS
                                              li4sa    n      o  N       RasnRS
                             B   M            uJHmu    l      N  I       seaasp
                             b   s            IIIII    I      I  I       aIABaI
                             v   e              //                       IIIIII
                             I   I                                         //

ACAAACTGTTTACTCTTTTTAAGAGTTAGCTGCATTCCTGCGGGAGGTACGCAAT    300
       ---+---------+---------+---------+---------+---------+---
          TGTTTGACAAATGAGAAAAAATTCTCAATGACGTAAGGACGCCCTCCATGCATGCGTTA
      241

E                   B
             F    c                   s                     N
             n    o    P              1M           B        l
             u    4    1              2aB    M     s        a
       M     w    H    5              8eb    w     p        I        E   E
       B     o    I    I              6Iv    o     M        I        s   C       E
       n     I    I    I              III    I     I        I        n   n   C   f
       b                                //                           B   B   n   f
       v                                                             I   I       I
       I                                                                             360

CAAAGCAGCAGGGCACGTTCGCAACACCTGCTTCAACTTCATGCACATTAGCAACAAGAT
       ---+---------+---------+---------+---------+---------+---
          GTTTCGTCGTCCCGTGCAAGCGTTGTGGACGAAGTTGAAGTACGTGTAATCGTTGTTCTA
      301
                             E  E
                             CnBn   C
                             AvusuPAvS                              E
                             li4p4slif                              cBS
               M     B       uJHCHtuJe              S         S     osc
               n     b       IIIIIIIII              n         f     Rar
               l     v         //                   e         e     IJF
               I     I                              I         I     III TGGGTAGTTGATTGTTGGGAGGATAGCTGCAGCTCCCTACGGAGTGAACTACAGTTCCA     420
       ---+---------+---------+---------+---------+---------+---
          ACCCATCAACTAACACCCCTCCTATCGACGTCGAGGGATGCCCTCACTTGATGTCAAGT
      361
```

FIG._1C

```
                    B
                    s
                    p
                    1H          S      H    C                    F HT  E
                    2g         Ba Ca             C               a hh  a
                    81         su ve   rMM v                     u aa  r
                    6A         p9 ii   lns i                     I III I
                    II         C6 JI   Olp J
                               II II   III I
                                /       /  /                      /

421
     GGGGGAGCACAGCAAGGGCCAATACCGGCTGTGAGGCGCGTAGCGGGAAGAGATGTATGG  480
     -----+---------+---------+---------+---------+---------+
     CCCCCTCGTGTCGTTCCCGGTTATGGCCGACACTCCGCGCATCGCCCTTCTCTACATACC
                                                                      M
                                                                      b
                                                                      o
                                                                      I
                                                                      I

C     M                                  S
     Av    s                    A             Ba     sFS    M
     li    e                    l    su  D    a3 P   aot    n
     uJ    I                    w    BA  n    BA n   Jky    l
     II                         I    II  I    II I   III    I
      /                                       /              /

481
     TAAGGGATAGCTGTTTAACCATTTGTAATGAATGGGATGTTGATCCTCCTTGAATAAT    540
     -----+---------+---------+---------+---------+---------+
     ATTCCCTATCGACAAATTGGTAAACATTACCTTACCCTACAACTAGGAGGAACCTTATTA
```

FIG._1D

```
        MBS                         M                         F
        asn      M      X           bB           T            n
        eaa      m      m           os           a            uS
        IAB      e      n           Ir           q            4p
        III      I      I           II           I            HI
                                                              II
                                                                        600
     ACGTATATAAGAAGATTTCATTCCAGTTGGAAAGCAATCGAGAAAACGCCGCCCAAATA
541  ----------+---------+---------+---------+---------+---------+
     TGCATATATTCTTCTAAAGTAGTCAACCTTTCGTTAGCTCTTTTGCGGCGGGTTTAT A                                                    B
            fBM       C          HB        NT   M                MBsM
            lsaP      v   p      is        rh   l                ssmc
            Iaem      i   l      np        ua   y                paAr
            IAIl      J   e      fM        II   I                IIII
            IIII      I   I      II                              ////
            ////
     CGCTTCGCCACGTGTAGCCCTGTATGGACTCGCGAAGCAGGTCTCCGGTCGGTGTCCAAG
601  ----------+---------+---------+---------+---------+---------+    660
     GCGAAGCGGTGCACATCGGGACATACCTGAGCGCTTCGTCCAGAGGCCAGCCACAGTTC S
     a
     u  D        M
     3  P        n                                                     MBS
     A  n        l                                                     asnB
     I  I        I                                                     eaab
                                                                       IABv
                                                                       IIII
                                                                       ////
     ATTGATCTAACTATTGAGTGAGGACTACTTACCGATTGATAGAATAATACGTATATAAG
661  ----------+---------+---------+---------+---------+---------+    720
     TAAACTAGATTGATAACTCACTCCTGATGAATGGCTAACTATCTTATTATGCATATATTC
```

*FIG._1E*

```
              F                          S                  T              H
              Cn           M             a                  sM             Ha           H
              Avu          b             uD         T       ps             he           i
              li4          o             3p         a       Ee             aI           n
              uJH          I             An         q       II             II           f
              III          I             II         I                                   I

AAGAAGCTGCTTGTGGAGTGATCTTTCTCGAAATGAATTAAGTAAGGCGCTATGTTCAG
721      ---------+---------+---------+---------+---------+---------+   780
         TTCTTCGACGAAACACCTCACTAGAAAGAGCTTACTTAATTCATTCCGCGATACAAGTC

A     D         MSM            C          M         E
              T l   r         npa            v          w         c        B
              T w   d         lee            i          o         o        sA
              i N   I         III            J          I         5        av
              I I   I                        I                    7        Ja
                                                                  I        II ATTCTGAACCAAAGCACTAGTTGAGTCTGAAGCCTTATGAGCAGAAGTAATAAATACCT
781      ---------+---------+---------+---------+---------+---------+   840
         TAAGACTTGGTTTCGTGATCAACTCCAGACTTCGGAATACTCGTCTTCATTATTTATGGA
```

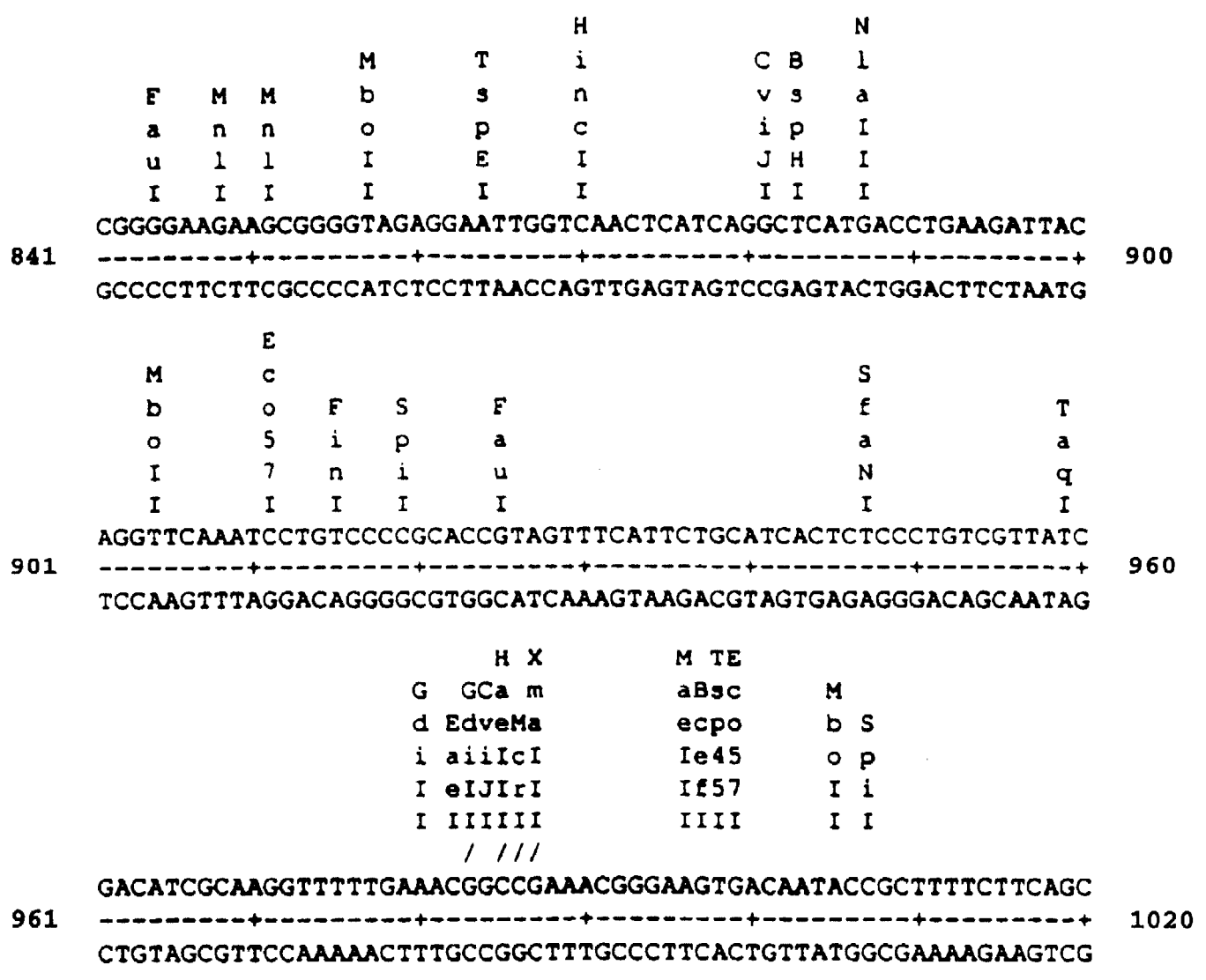

ATATAAATGCAATGATTACCTTTTTCGAAAAATGTCCACTTTTTGTCATAATCTCACTC
1021  ------+---------+---------+---------+---------+---------+  1080
      TATATTTACGTTACTAATGAATGCTTTTTACAGGTGAAAAACAGTATTAGAGTGAG

S  H
                                                            aCa
                                                            uve
                                                            9iI
                                               C            6JI
                                               Av           III
         C    C                                li            /
         vDE  Av                                uJ
         ids  li                                II
         Jep  uJ                                 /
         III  II
          /   /

CTACTGAATGTAAAGTAAGTTAGTGTAATAAGTTTCTTTCTTTTAGCTTTTTTACTAATGGCCC
1081  ------+---------+---------+---------+---------+---------+  1140
      GATGACTTACATTTCAATCACATTATTCAAAGAAAGAAAATCGAAAAATGATTACCGGG

N   S
                                                           l   a  E
                                                    BD     a   uDsMX
                                                    sr     I   3ppab
                                                    md     I   An3ea
                                                    AI     I   IIIII
                                                    II      \ / /

ATATTTGGCTAAGCTGGTTTTCTAACAACCAACATTGTTACGAACCATGAGACATCTA
1141  ------+---------+---------+---------+---------+---------+  1199
      TATAAACCGATTCGACCAAAAGATTGTTGGTTGTAACAATGCTTGGTACTCTGTAGAT
```

FIG._1H

```
              T
              a
              qT               T
         T    Is          C    s
    N    s    Ip          vM   p
    d    p    -E          ia   E
M   e    E    2I          Je   I
s   I    I    I           II   I
e
I
GAGAAGTTAAAAATTCCATATGAATTCCAGTATGGGTGGCTAGGTGTCAAAATTACAATA
-----+---------+---------+---------+---------+---------+    1259
CTCTTCAATTTTTAAGGTATACTTAAGGTCATACCCACCGATCCACAGTTTAATGTTAT
1200

M
         M  T                                     s    M
         a  s                            B        e    n
    R    e  p      H                     s        1    1
    s    1  1      p                     m   M    I    I
    a    I  I      h                     A   s    I    I
    I    I  I      I                     I   e
                                              1
                                              I
AAATCAAATGTACCTAACGATGAAGTGACGAAAAAGTCTCACCTATCATTAAAGGGGAA
-----+---------+---------+---------+---------+---------+    1319
TTTAGTTTACATGGATTGCTACTTCACTGCTTTTTCAGAGTGGATAGTAATTTCCCCTT
1260

M              M              M
M                  n              n              n
n                  1              1              1
1                  I              I              I
I
ATAGAGGGAAAGAGGGAAAAAAGAGGGGAAAAGAGGGAAATAGAGGGAAAGAGGAAAAA
-----+---------+---------+---------+---------+---------+    1379
TATCTCCCTTTCTCCCTTTTTTCTCCCCTTTTCTCCCTTTATCTCCCTTTCTCCTTTTT
1320
```

FIG._1I

```
                       M            M              M                   T
                       n            n              n                   s
                       l            l              l                   p
                       I            I              I                   E
                                                                       I
      AAAGAGGGGAAAGGGAAATAGAGGGGAAAGAGGAAAAAAGAGGTGGAAATTGACCG          1439
      ---------+---------+---------+---------+---------+---------+
      TTTCTCCCCTTTCCCCTTTATCTCCCCTTTCTCCTTTTTTCTCCACCTTTAACTGGC
              T                    T
              a                   Ms
              q                   fp
              I                   eE
              -                   II
              I                    I
      1380                       1440

AGAAAATAATGCTTTGTGAACCCAATTGCTTTGACAAAATAAAGAAGAAGCAAAATCT        1499
      ---------+---------+---------+---------+---------+---------+
      TCTTTTATTACGAAACACTTGGGTTAACGAAACTGTTTTATTTCTTCTTCGTTTTAGA
                      S                                                N
                     BB     a          M                               l
                     gs    Du          b                               a    X
                     lt   p3           o                               I    c
                     IY   nA           I                               I    m
                     II   II           I                               I    I
                          //                                                /
              T
              s        E
              p        a
              E        r
              I        I
      1440                       1500

CATTCAATTTGAAATAGAAGATCTCTATGCCCCTGTTCTTGGTTTCTCCCATGCTT          1559
      ---------+---------+---------+---------+---------+---------+
      GTAAGTTAAACTTTATCTTCTAGAGATACGGGGACAAGAACCAAAGAGGGTACGAA

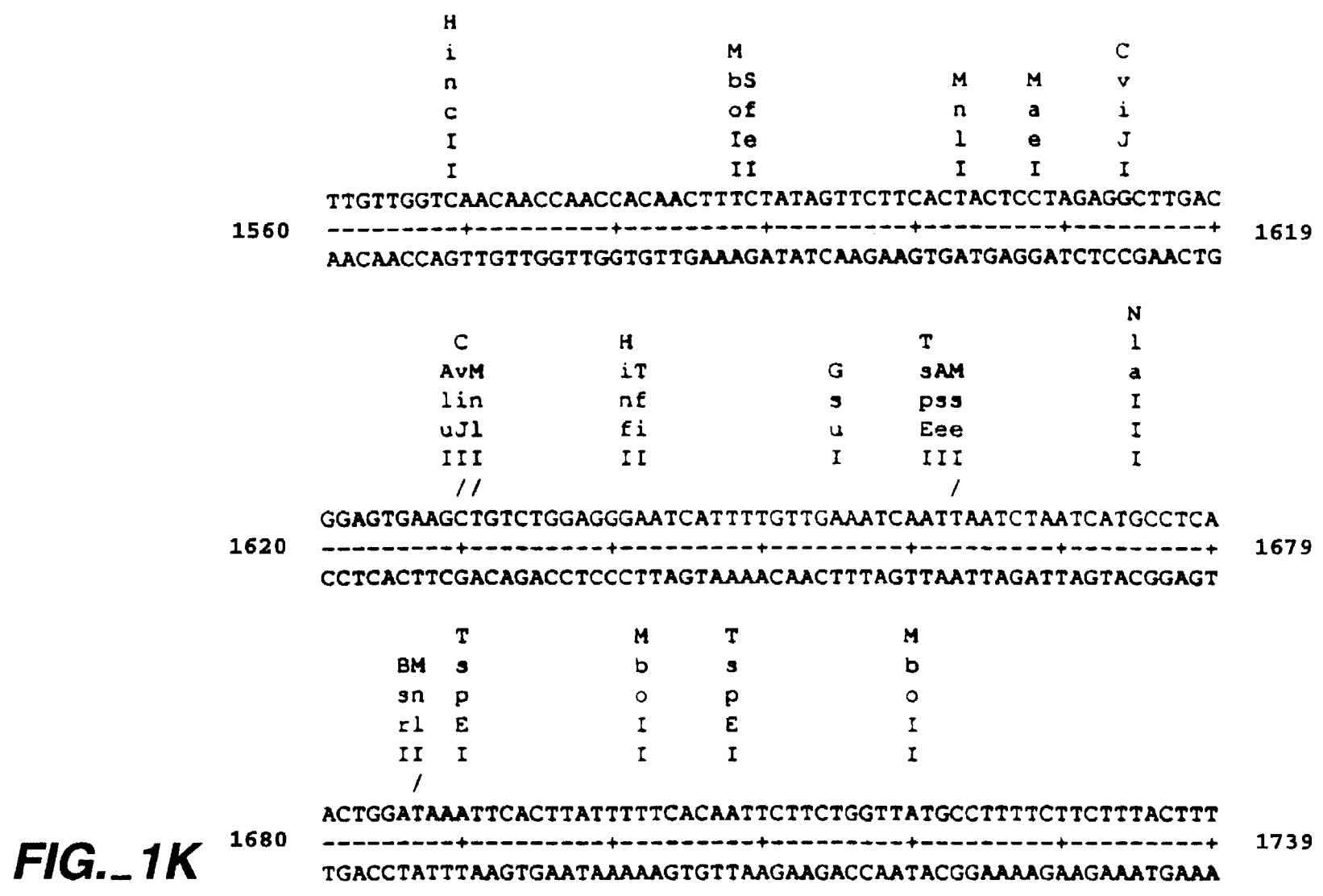

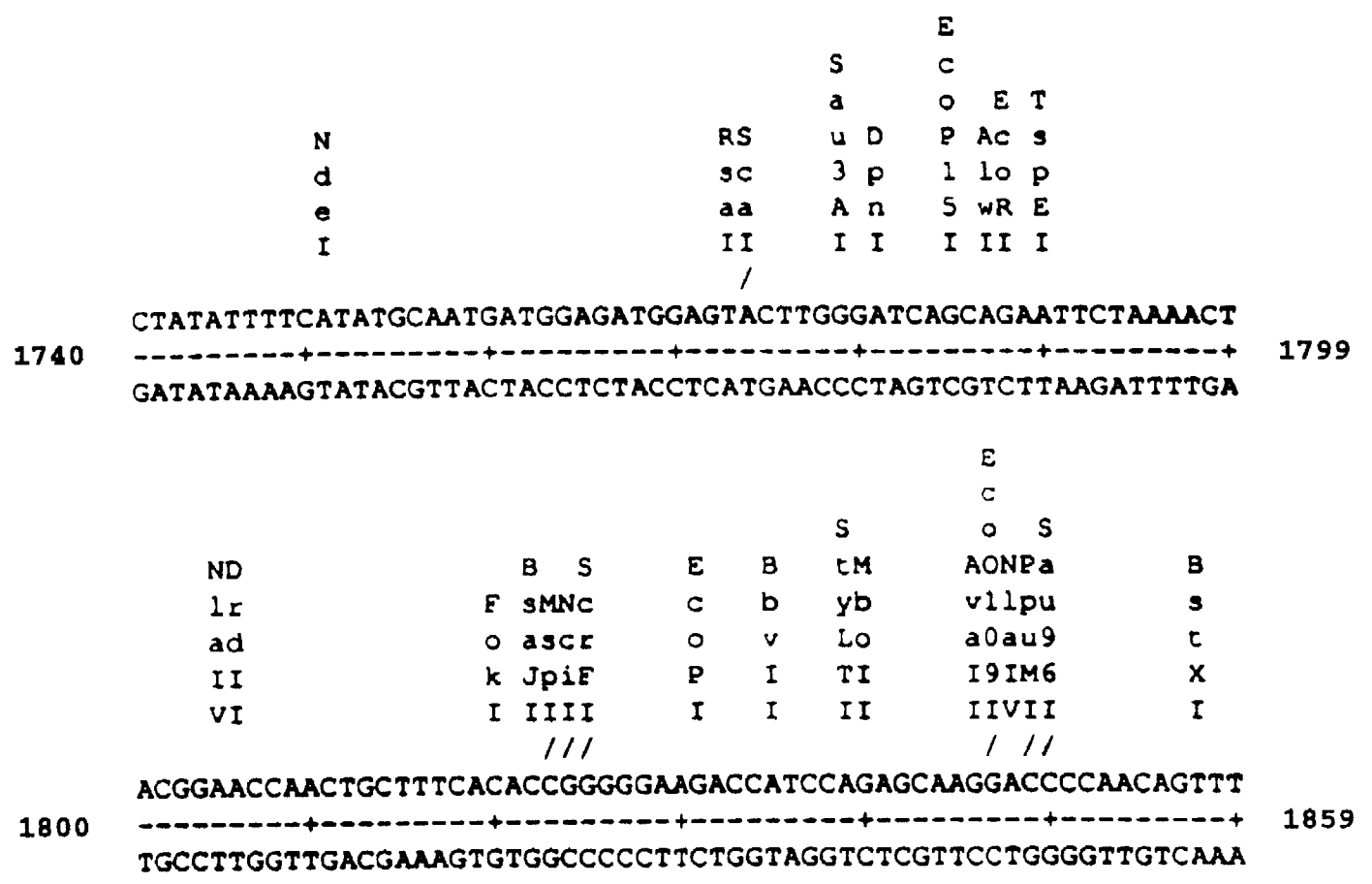

```
         S                                                    B         M                                   B
        BB  a                  M                              s         a                                   s  t  B
        gsDu                   b                              r         e                                   a  t  B
        ltp3                   o                              I         I                                   u  3  A
        IYnA                   I                                                                            3     I
        IIII                   I                                                                            A     I
        ////                   /                                                                            I     I
                                                                                                           //
1860    GGAAGATCTCTTGAGAAAAGTTTTAGCACTGGTGTATCCTATATGTATGCTAGTTTATT    1919
        --------+---------+---------+---------+---------+---------+
        CCTTCTAGAGAACTCTTTTCCAAAATCGTGACCACATAGGATATACATACGATCAAATAA H   H
                         Ca  i                           M
                    B    ve  SAnT                        n
                    c    iI  acca                        l
                    e    JI  lcIq                        I
                    f    II  IIII                        I
                    I    //  ////                        /
1920    CGAAGTATCCAATGGTGTAAGGCCGTCGACTTATTGGGAAAAGGAGGAAAATCACTTT    1979
        --------+---------+---------+---------+---------+---------+
        GCTTCATAGGGTTACCACATTCCGGCAGCTGAATAACCCTTTTCCTCCTTTTAGTGAAA C
                   D     M  vB
                   p     n  is
                   n     l  Ji
                   I     I  II
                   I
1980    GATCTCTGTTTCGGAGAAATAAGTGGCTCACGAGGAATGGAAAGAAACATATTATATAA    2039
        --------+---------+---------+---------+---------+---------+
        CTAGAGAACAAAGCCTCTTTATTCACCGAGTGCTCCTTACCTTTCTTTGTATATATATT
```

FIG._1M

```
                                    S
                                    a
              M         B           u D     A     T
              n         s           3 p  A  l     s  T
              l         r           A n  l  w     p  p
              I         I           I I  I  I     I  E
                                                  I

TATATCGAAGTCCTCTCCTTCAAATACTGGAAGGTGGATCACTTGTAGGAATTGTAGGAA   2099
2040 ---------+---------+---------+---------+---------+---------+
    ATATAGCTTCAGGAGAGAAGTTTATGACCTTCCACCTAGTGAACATCCTTAACATCCTT

T
    a
    q
    I

N         N      H                       S
              l         l   BC a                       t
              a  X R    c s EaBsvHeSM                H i T   S
              I  c s    s s alaaiAltw                i n f   e
              I  m a    e l eIlJJelyo                n f i   e
              I  I I    I I IIIIIIIII                I I I   I
                              ///

TGACATAATGCTAATCCATGTTGTACATGGCCAAGGAAGCATAAATGATTCTTTCATTC   2159
2100 ---------+---------+---------+---------+---------+---------+
    ACTGTATTACGATTAGGTACAACATGTACCGGTTCCTTCGTATTTTACTAAGAAAGTAAG

B
    E                                               M  s
    c        M                                      n  h  p
    o        n                                   4F /a  l  C
    R        l                                   3u  l  a  I
    I        I                                   II II  I  I
                                                          /

TATAGATACCTCTGGTAGGTAAAGCACTCTACTGTGCTTTATTGAAAGTTCCCATGCGGG   2219
2160 ---------+---------+---------+---------+---------+---------+
    ATATCTATGGAGACCATCCATTCGTGAGATGACACGAAATAACTTTCAAGGGTAGCGCC
```

FIG. – 1N

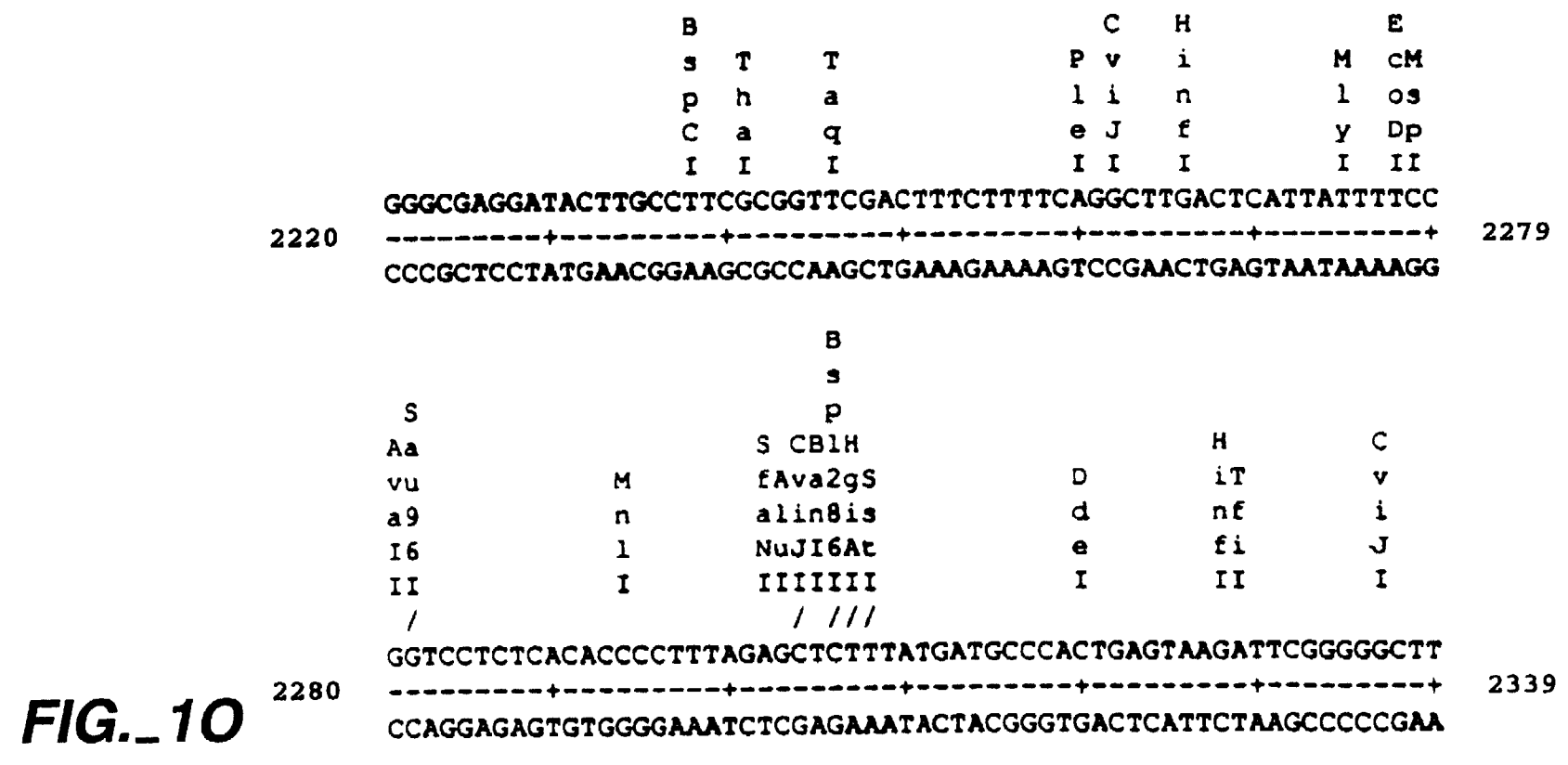

FIG._10

```
         S    B  C       N                                                        M
         M N c H s A v   F   B s S   E N M          B      s T  E                 a  E M
         s c r h p l i   a   s D p a S T   s l b    s T    m a  a                 e  a n
         p i F a C u J   u   a s B c p h   p a o    A q    r    r                 r  r l
         I I I   I I I   I   J a I I i a   3 I I    I I    I I  I                 I  I I
          / /      / /       I I I I I I   I V I                                     / /
                                 / /       / /
     CCCGGCGCAGAAGCTCATTCTGAACCGCGGGAACCTTCGTCTCTTCGACACAAACGTTTT
     ----+----|----+----|----+----|----+----|----+----|----+----|
     GGGCCGCGTCTTCGAGTAAGACTTGGCGCCCTTGGAAGCAGAGAAGCTGTGTTTGCAAAA
2340                                                                   2399

C      M        B B B  N  a
                v      M b  A   s a s D l H u
                i      n  o l   a m t p a p 3
                J      l  l w   B H Y n I h A
                I      I  I I   I I I I V I I
                                       / / /
     ATGAAGAGGCTGATGGTGATGAGGATCC
     ----+----|----+----|----+--        2427
     TACTTCTCCGACTACCACTACTCCTAGG
2400
```

FIG._1P

ENZYMES THAT DO CUT:

| | | | | | | |
|---|---|---|---|---|---|---|
| AccI | AflIII | AluI | AlwI | AlwNI | AseI | AvaI | AvaII |
| BalI | BamHI | BanII | BbvI | BbvII | BcefI | BglII | BpuI0I |
| BsaI | BsaAI | BsaBI | BsaJI | BsiI | BsmI | BsmAI | Bsp1286I |
| BspCI | BspHI | BspMI | BsrI | BstBI | BstXI | BstYI | Cfr10I |
| CviJI | DdeI | DpnI | DrdII | DsaI | EaeI | EarI | Eco57I |
| EcoBI | EcoDI | EcoNI | EcoO109I | EcoPI | EcoP15I | EcoRI | EcoRII |
| EcoR124/3I | EspI | Esp3I | FauI | FinI | Fnu4HI | FokI | GdiII |
| GsuI | HaeI | HaeIII | HgiAI | HhaI | HincII | HinfI |
| HphI | MaeI | MaeII | MboII | McrI | MfeI | MlyI |
| MmeI | MnlI | MseI | MspI | MwoI | NciI | NcoI | NdeI |
| NheI | NlaIII | NlaIV | NruI | NspBII | PleI | PmlI | PpuMI |
| PstI | RsaI | SacII | SalI | Sau96I | Sau3AI | ScaI | ScrFI |
| SfaNI | SfeI | SnaBI | SpeI | SplI | SpII | SstI | StyI |
| StyLTI | StySJI | TaqI | TaqII-1 | TaqII-2 | TfiI | ThaI | Tsp45I |
| TspEI | TthIIII | XbaI | XcmI | XmaIII | XmnI |

ENZYMES THAT DO NOT CUT:

| | | | | | | |
|---|---|---|---|---|---|---|
| AatII | AflII | AgeI | AhaII | ApaI | ApaLI | AvrII | BanI |
| BcgI | BclI | BglI | BspGI | BspMII | BssHII | BstEII | Bsu36I |
| CfrAI | ClaI | DraI | DraIII | DrdI | EciI | Eco47III | EcoAI |
| EcoDXXI | EcoEI | EcoKI | EcoR124I | EcoRV | FseI | FspI | HgaI |
| HgiEII | HindIII | HinfIII | HpaI | KpnI | MluI | NaeI | NarI |
| NotI | NsiI | NspI | PflMI | PshAI | PvuI | PvuII | RleAI |
| RsrII | SfiI | SgrAI | SmaI | SnaI | SphI | SspI | StuI |
| StySBI | StySPI | StySQI | TthIIII | UbaII05I | UbaII08I | XhoI |

FIG._1Q

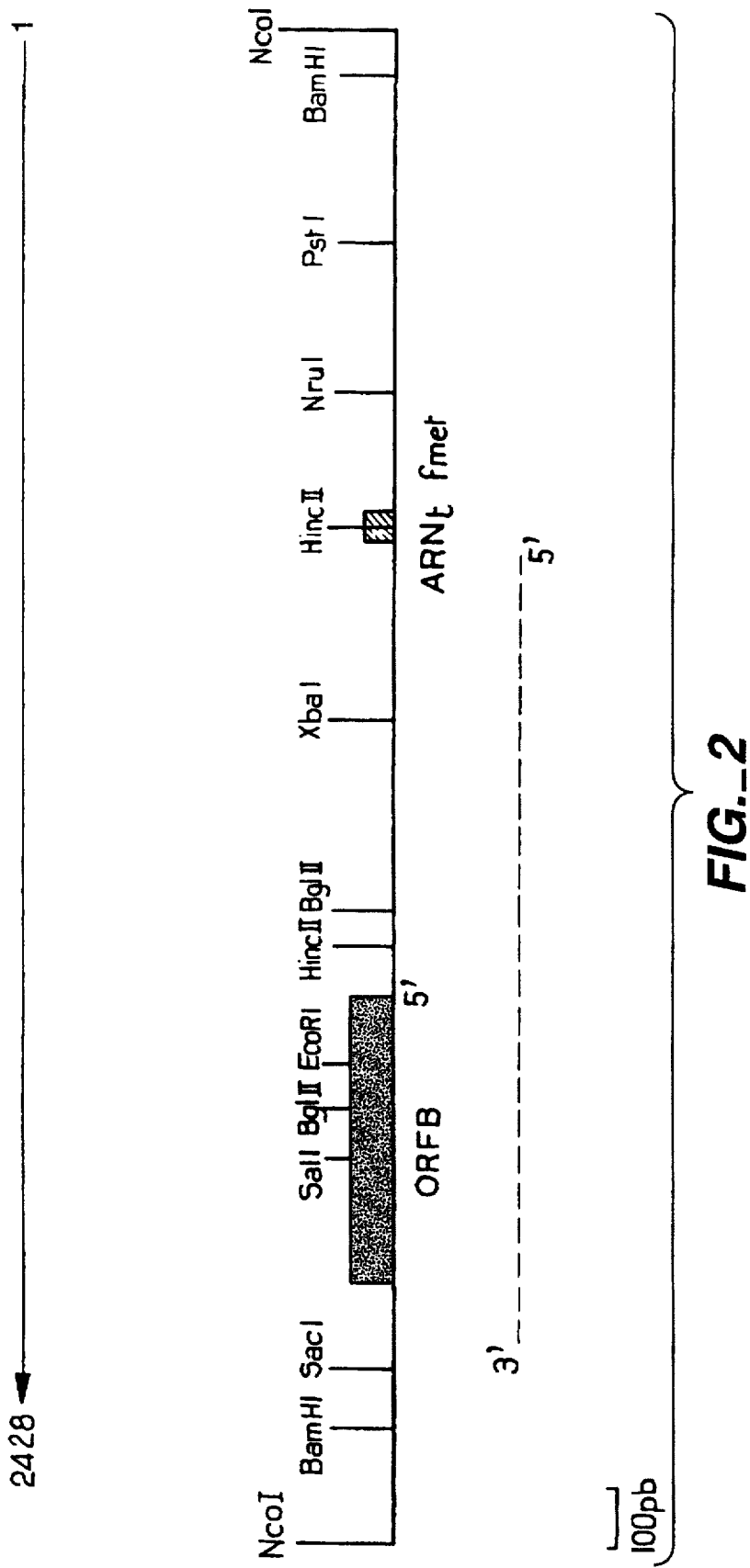
FIG._2

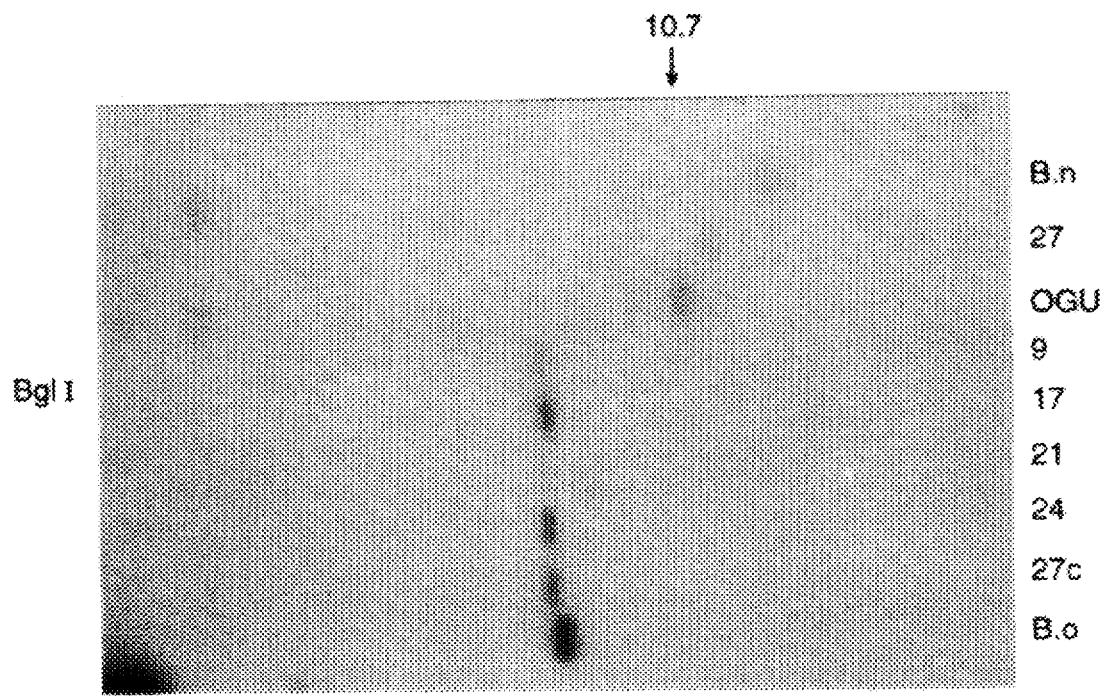
FIG._3A
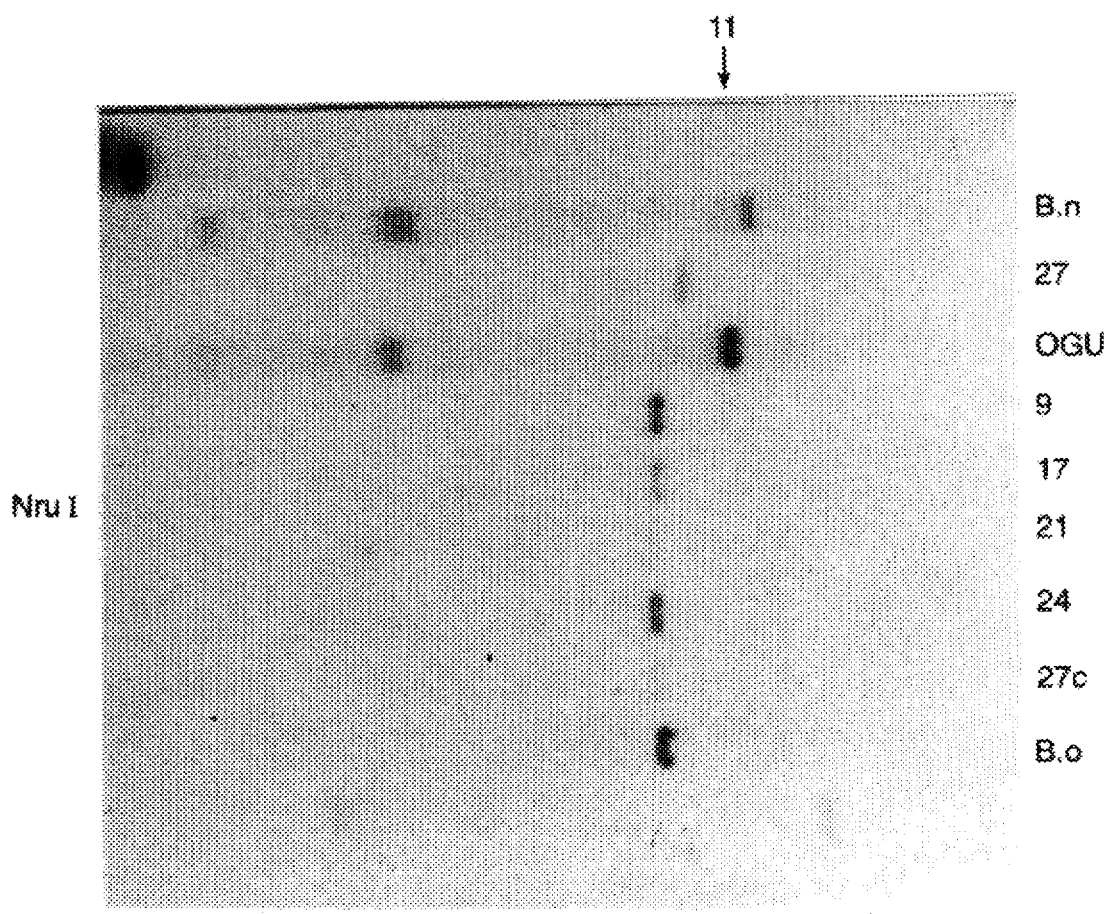
FIG._3B

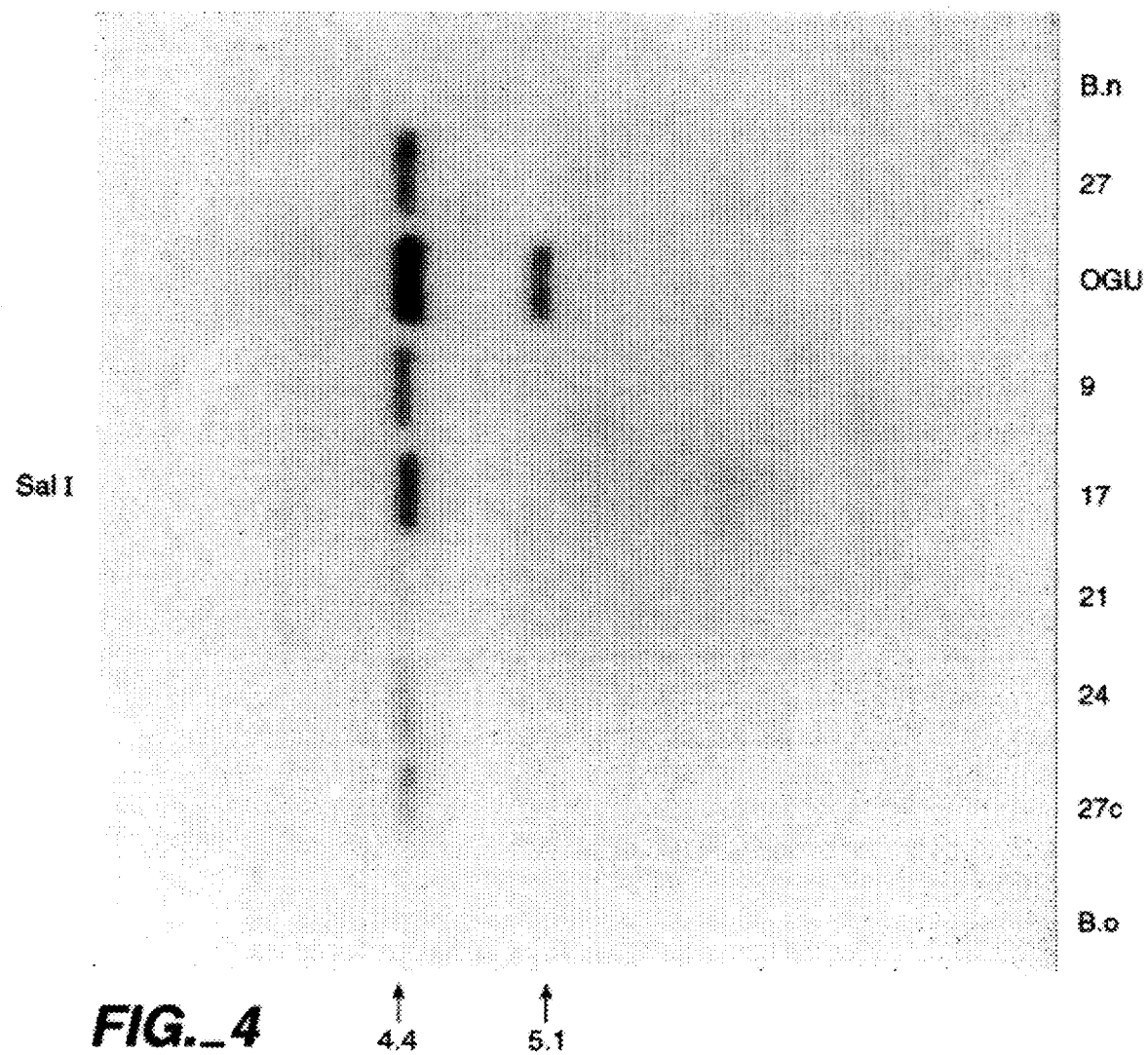
FIG._4

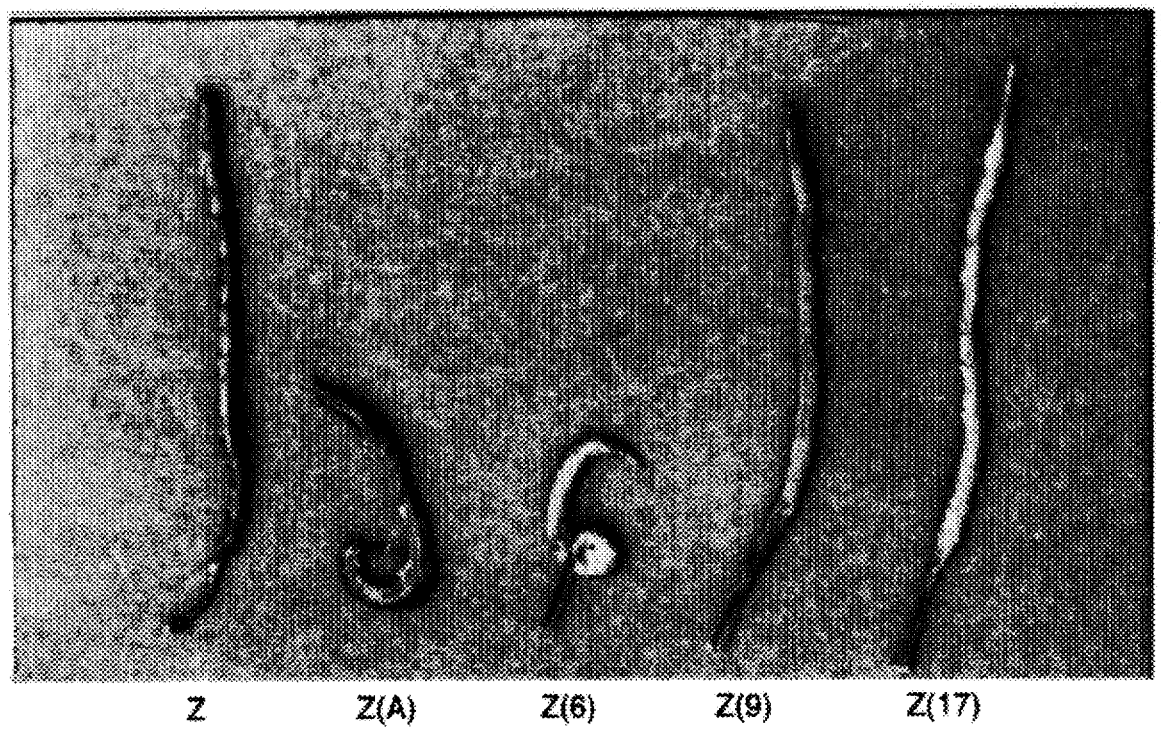
FIG._5

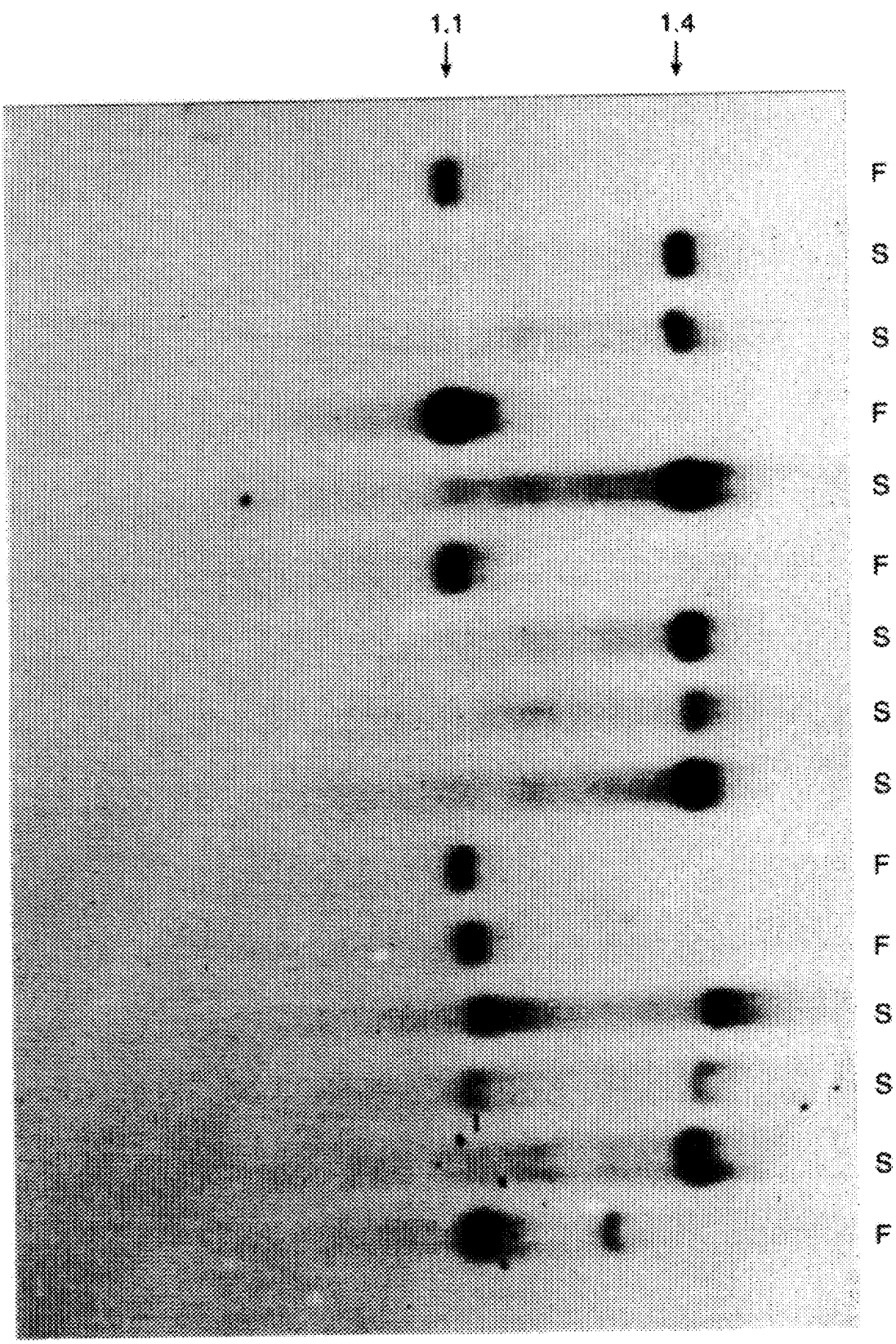
FIG._6

5,789,566

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 2427 base pairs
( B ) TYPE: nucleic acid
( C ) STRANDEDNESS: double ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:1:

```
CCATGGACAA TAATCTTAGT CGGAGTCAAA TTCCTTACCT TTCCACCCAA AGCTGAACAT    60
ATCCGCACAG ATATTCCATT TTTTTATTG  AGGATCCATT TTCGAACTGA ACTACTCATG   120
CTTAGGCAAA ACAAGCAAGG GAGTTGTTAA TAAGGAGCTA GCTACAGTGC TGCGGAGGGT   180
TCCGTGCTTA TTAAGGAGCC GGGCAGCTAC GCAACACTTC CTTGCAACTC ATACCTACTA   240
ACAAACTGTT TACTCTTTTT TAAGAGTTAG CTGCATTCCT GCGGGAGGTA CGTACGCAAT   300
CAAAGCAGCA GGGCACGTTC GCAACACCTG CTTCAACTTC ATGCACATTA GCAACAAGAT   360
TGGGTAGTTG ATTGTTGGGA GGATAGCTGC AGCTCCCTAC GGGAGTGAAC TACAGTTCCA   420
GGGGGAGCAC AGCAAGGGCC AATACCGGCT GTGAGGCGCG TAGCGGGAAG AGATGTATGG   480
TAAGGGATAG CTGTTTAACC ATTTGTAATG GAATGGGATG TTGATCCTCC TTGGAATAAT   540
ACGTATATAA GAAGATTTTC ATTCCAGTTG GAAAGCAATC GAGAAACGC  CGCCCAAATA   600
CGCTTCGCCA CGTGTAGCCC TGTATGGACT CGCGAAGCAG GTCTCCGGTC GGTGTCCAAG   660
ATTTGATCTA ACTATTGAGT GAGGACTACT TACCGATTGA TAGAATAATA CGTATATAAG   720
AAGAAGCTGC TTTGTGGAGT GATCTTTCTC GAAATGAATT AAGTAAGGCG CTATGTTCAG   780
ATTCTGAACC AAAGCACTAG TTGAGGTCTG AAGCCTTATG AGCAGAAGTA ATAAATACCT   840
CGGGGAAGAA GCGGGGTAGA GGAATTGGTC AACTCATCAG GCTCATGACC TGAAGATTAC   900
AGGTTCAAAT CCTGTCCCCG CACCGTAGTT TCATTCTGCA TCACTCTCCC TGTCGTTATC   960
GACCTCGCAA GGTTTTGAA  ACGGCCGAAA CGGGAAGTGA CAATACCGCT TTTCTTCAGC  1020
ATATAAATGC AATGATTACC TTTTTCGAAA AATTGTCCAC TTTTTGTCAT AATCTCACTC  1080
CTACTGAATG TAAAGTTAGT GTAATAAGTT TCTTTCTTTT AGCTTTTTA  CTAATGGCCC  1140
ATATTTGGCT AAGCTGGTTT CTAACAACC  AACATTGTTT ACGAACCATG AGACATCTAG  1200
AGAAGTTAAA AATTCCATAT GAATTTCAGT ATGGGTGGCT AGGTGTCAAA ATTACAATAA  1260
AATCAAATGT ACCTAACGAT GAAGTGACGA AAAAAGTCTC ACCTATCATT AAAGGGGAAA  1320
TAGAGGGGAA AGAGGAAAAA AAAGAGGGGA AAGGGGAAAT AGAGGGGAAA GAGGAAAAA   1380
AAGAGGGGAA AGGGGAAATA GAGGGGAAAG AGGAAAAAAA AGAGGTGGAA AATGGACCGA  1440
GAAAATAATG CTTTGTGAAC CCAATTGCTT TGACAAAAAT AAAGAAAGAA GCAAAATCTC  1500
ATTCAATTTG AAATAGAAGA GATCTCTATG CCCCCTGTTC TTGGTTTTCT CCCATGCTTT  1560
TGTTGGTCAA CAACCAACCA CAACTTTCTA TAGTTCTTCA CTACTCCTAG AGGCTTGACG  1620
GAGTGAAGCT GTCTGGAGGG AATCATTTTG TTGAAATCAA TTAATCTAAT CATGCCTCAA  1680
CTGGATAAAT TCACTTATTT TTCACAATTC TTCTGGTTAT GCCTTTCTT  CTTACTTTC   1740
TATATTTTCA TATGCAATGA TGGAGATGGA GTACTTGGGA TCAGCAGAAT TCTAAAACTA  1800
CGGAACCAAC TGCTTTCACA CCGGGGGAAG ACCATCCAGA GCAAGGACCC CAACAGTTTG  1860
GAAGATCTCT TGAGAAAAGG TTTTAGCACT GGTGTATCCT ATATGTATGC TAGTTTATTC  1920
GAAGTATCCC AATGGTGTAA GGCCGTCGAC TTATTGGGAA AAAGGAGGAA ATCACTTTG   1980
ATCTCTTGTT TCGGAGAAAT AAGTGGCTCA CGAGGAATGG AAAGAAACAT ATTATATAAT  2040
ATATCGAAGT CCTCTCCTTC AAATACTGGA AGGTGGATCA CTTGTAGGAA TTGTAGGAAT  2100
GACATAATGC TAATCCATGT TGTACATGGC CAAGGAAGCA TAAAATGATT CTTTCATTCT  2160
```

-continued

| ATAGATACCT | CTGGTAGGTA | AAGCACTCTA | CTGTGCTTTA | TTGAAAGTTC | CCATCGCGGG | 2220 |
|---|---|---|---|---|---|---|
| GGCGAGGATA | CTTGCCTTCG | CGGTTCGACT | TTCTTTTCAG | GCTTGACTCA | TTATTTTCCG | 2280 |
| GTCCTCTCAC | ACCCCTTTAG | AGCTCTTTAT | GATGCCCACT | GAGTAAGATT | CGGGGGCTTC | 2340 |
| CCGGCGCAGA | AGCTCATTCT | GAACCGCGGG | AACCTTCGTC | TCTTCGACAC | AAACGTTTTA | 2400 |
| TGAAGAGGCT | GATGGTGATG | AGGATCC | | | | 2427 |

DNA SEQUENCE IMPARTING CYTOPLASMIC MALE STERILITY, MITOCHONDRIAL GENOME, NUCLEAR GENOME, MITOCHONDRIA AND PLANT CONTAINING SAID SEQUENCE AND PROCESS FOR THE PREPARATION OF HYBRIDS

CROSS REFERENCE TO RELATED APPLICATIONS

This application is a continuation of U.S. application Ser. No. 08/030,083, filed as PCT/FR91/00741 Sep. 20, 1991 published as WO92/05251 Apr. 2, 1992, now abandoned.

The present invention relates to a biological material possessing a male sterility which is useful for the development of hybrid varieties of species of agronomic importance.

It relates especially to a plant belonging to the Cruciferae family, in which the cytoplasm of the cells contains organelles possessing nucleotide sequences conferring a male sterility and good agronomic characteristics.

The development of hybrid varieties can be facilitated or made possible by the use of a cytoplasmic male sterility system. The hybrids are obtained by cross-fertilisation between two parent populations, one performing the role of male, the other of female. One of the stumbling blocks encountered when it is desired to obtain hybrid varieties of uniform quality by sexual crossing on self-fertile species is the capacity of the plant to self-pollinate. Male sterility systems enable female plants to be obtained which are incapable of self-fertilisation and from which, after pollination, the seeds, which are all hybrids, can be harvested directly without resorting to laborious techniques such as castration of the flowers.

The genetic determinants of male sterility include those which are carried by the cytoplasm. At each sexually produced generation, they are transmitted exclusively by the mother. 100% of male-sterile offspring are thereby produced at each generation with a cytoplasmic male sterility (CMS) system. These genetic determinants are carried by the genome of the mitochondria.

A suitable cytoplasmic male sterility system in Cruciferae is defined by the following characteristics:

1) The male sterility must be total, that is to say there must be no pollen production regardless of the culture conditions and regardless of the line which it is desired to use as a female parent. Were this not the case, the seeds harvested from these female plants would be derived in part from self-fertilisation and would hence not be of the F1 hybrid type.

2) The production of these seeds must be carried out taking advantage of the natural pollen vectors, that is to say, in the case of these species, Hymenoptera, Diptera and wind. The pollen must be transported from the pollinating plants to the male-sterile (female) plants. In fact, only insects can effect this transport at a distance in Cruciferae.

The female plants must consequently be sufficiently attractive to the insects which come and collect the nectar in them. The morphology of the flowers must force the insect to perform this task via the top of the flower so that its thorax, principally, comes into contact with the stigma. In practice, this amounts to a situation where the base of the petals has to form a kind of tube around the base of pistil.

3) The morphology of the female organs (pistil) must be identical to that of a fertile plant, especially one single pistil per flower and rectilinear in shape. In effect, male sterilities often result also in a feminisation of the anthers, which are transformed into pseudopistils, and even in transformation of the nectaries into complete flowers. Sometimes the pistil or pistils thereby produced are also deformed. All these abberations do not permit good seed production, and this may be regarded as equivalent to some degree of female sterility.

4) For the production of F1 hybrid varieties in the species from which the seeds are harvested, such as colza or mustards, it is essential that the male parent of the hybrid completely negates the effect of the male-sterile cytoplasm, so that the hybrid plants are readily pollinated.

In Cruciferae, the first case of male-sterile cytoplasm or CMS was described by Ogura (1968) in the radish, Raphanus sativus. Bannerot (1974, 1977) transferred the Ogura cytoplasm in Brassicae, thereby obtaining plants which possess a cytoplasmic male sterility. These same plants did not possess satisfactory agronomic characteristics (chlorosis on lowering temperatures, poor female fertility), resulting in a poor yield making them unsuitable for commercial use.

In Cruciferae, to avoid this chlorosis, the nuclear and chloroplast genomes of one and the same genus should be combined in the same cell. Thus, Brassica plants possessing one of the chloroplast genomes of Brassicae no longer exhibit chlorosis. If they possess the whole of the Ogura mitochondrial genome, they exhibit total cytoplasmic male sterility but, however, the flowers will have an aberrant morphology making it impossible for them to be pollinated by the natural vectors.

In addition, for species in which the interest lies in the seeds, it is appropriate to restore the male fertility of hybrid varieties which are marketed by means of nuclear genes known as restorer genes.

It is difficult to restore the male fertility of a plant possessing the whole of the Ogura mitochondrial genome, since it is necessary to bring about the simultaneous participation of several restorer genes.

We set out to obtain a suitable male sterility system by removing the genes responsible for the undesirable characters of the Ogura cytoplasm while retaining a male sterility which is effective and easy to restore.

Thus, the present invention relates to a DNA sequence, which we shall refer to as Ogura sterility DNA sequence, characterised in that:

a) it is carried by a DNA sequence bounded by nucleotides 928 and 2273 in FIG. 1 (SEQ ID NO: 1), or b) it possesses an at least 50% homology with the said sequence mentioned in a), and confers, when it is present in the mitochondrial genome of a plant, a cytoplasmic male sterility on the said plant.

In particular, the subject of the present invention is an Ogura sterility DNA sequence, characterised in that:

c) it is carried by the sequence bounded by nucleotides 928 and 1569 in FIG. 1 (SEQ ID NO: 1), or d) it possesses an at least 50% homology with the said sequence mentioned in c), and in that it is transcribed to RNA in the mitochondria of male-sterile plants.

In what follows, reference will be made to the following figures:

FIG. 1: Nucleotide sequence (SEQ ID NO: 1) of the Ogura radish mitochondrial DNA fragment carrying the CMS character.

FIG. 2: Restriction map of the mitochondrial DNA fragment described in FIG. 1.

FIGS. 3(a) and (b): Electrophoresis of mitochondrial DNA after digestion with BglI (3a) and NruI (3b). The bands revealed correspond to a hybridisation with a Cox1 probe (Hiesel et al. 1987).

FIG. 4: Electrophoresis of mitochondrial DNA after SalI digestion. The bands revealed correspond to a hybridisation with a probe bounded by nucleotides Nos. 389 and 1199 of the sequence (SEQ ID NO: 1) described in FIG. 1.

FIG. 5: Fruits produced by cabbage plants carrying different cytoplasmic genomes.

FIG. 6: Electrophoresis of mitochondrial RNA. The bands revealed correspond to a hybridisation with a probe, an EcoRI-BamHI fragment, including a portion of the sequence referred to as ORF B.

The Ogura sterility DNA sequence is defined in relation to the sequence bounded by the numbers 1 and 2428 in FIG. 1 (SEQ ID NO: 1). It is carried by a transcribed sequence whose 3' and 5' ends are joined by a broken line in FIG. 2, and which is observed only in male-sterile plants. ORF B corresponds to an open reading frame; this designation was given on the basis of the observed homology with a sequence described by Brennicke. In FIG. 2, the sequence corresponding to one of the two formylmethionine transfer RNA genes is shown shaded.

The DNA sequence bounded by the nucleotides numbered 928 and 2273 in FIG. 1 (SEQ ID NO: 1) corresponds to a transcript which can be visualised by molecular hybridisation (1.4) as seen in FIG. 6. In this FIG. 6, each well corresponds to a fertile plant (F) or male-sterile plant (S). Only the male-sterile plants synthesise a transcript of approximately 1,400 bases. This transcript begins at position 928 ($\pm$10 bases) of the sequence (SEQ ID NO: 1) in FIG. 1 and ends at position 2273 ($\pm$5) (transcription initiation and termination can take place at various positions in plant mitochondria).

Preferably, the present invention relates to a cytoplasm containing a DNA sequence possessing an at least 50% homology with the sequence bounded by nucleotides 928 and 2273 in FIG. 1 (SEQ ID NO: 1) conferring the CMS character, or a cytoplasm containing a DNA sequence possessing an at least 50% homology with the sequence bounded by nucleotides 928 and 1569 in FIG. 1 (SEQ ID NO: 1), and transcribed to RNA, conferring the CMS character and characterised in that it:

contains chloroplasts of the same species as the nuclear genome or of another species but which are compatible with this nuclear genome, does not contain all or part of one or other (or both) fragment(s) of the Ogura mitochondrial genome, defined below:

carrying one of the two formylmethionine transfer RNA genes used for translation initiation, carrying the Cox1 gene coding for the subunit No. 1 of cytochrome oxidase.

The absence of these fragments, referred to as "undesirable sequences", is necessary in order to obtain mitochondrial genomes corresponding to a male sterility of good quality, corresponding to the 4 characteristics defined above.

According to another of its aspects, the invention relates to a recombinant plant nuclear or mitochondrial genome, characterised in that it contains an Ogura sterility DNA sequence:

a) which is carried by a DNA sequence bounded by nucleotides 928 and 2273 of the sequence (SEQ ID NO: 1) shown in FIG. 1, or b) which possesses an at least 50% homology with the said sequence mentioned in a), and confers, when it is present in the cytoplasm of a plant, a cytoplasmic male sterility on the said plant.

In particular, one of the subjects of the present invention is a recombinant plant nuclear or mitochondrial genome, characterised in that it contains an Ogura sterility DNA sequence, c) which is carried by a sequence bounded by the nucleotides numbered 928 and 1569 in FIG. 1 (SEQ ID NO: 1), or d) which possesses an at least 50% homology with the said sequence mentioned in c), and confers, when it is present in the cytoplasm of a plant and is transcribed to RNA, a cytoplasmic male sterility on the said plant.

A nuclear or mitochondrial genome according to the invention can be characterised in that the said recombinant mitochondrial genome is devoid of all or part of the Ogura genome fragments:

carrying one of the two formylmethionine transfer RNA genes used for translation initiation, carrying the Cox1 gene coding for the subunit No. 1 of cytochrome oxidase, or in which the said fragments are inactive.

More specifically, a recombinant mitochondrial genome according to the invention may be characterised:

1) in that it is devoid of all or part of an approximately 10.7-kb fragment after BglII digestion or of an approximately 11-kb fragment after NruI digestion, which fragments carry the Cox1 gene.

This is demonstrated, in particular, in FIG. 3, by molecular hybridisation with a probe carrying the Cox1 sequence.

2) in that it is devoid of all or part of a 5.1-kb fragment after SalI digestion or of an approximately 15-kb fragment after NruI digestion or of an approximately 18.5-kb fragment after BglII digestion, which fragments carry one of the two formylmethionine transfer RNA genes.

This demonstrated, in particular, in FIG. 4, by molecular hybridisation with a probe bounded by nucleotides Nos. 389 and 1199 of the sequence (SEQ ID NO: 1) described in FIG. 1.

In FIGS. 3 and 4, the genotypes designated by figures correspond to plants possessing a suitable cytoplasmic male sterility system.

| GENOTYPES | CHLOROPLASTS | MITOCHONDRIA |
|---|---|---|
| B. n | B. napus | B. napus |
| 27 | B. napus | B. napus/Ogura |
| OGU. | R. sativus (OGU) | R. sativus (OGU) |
| 9, 17, 21, 24, 27c | B. oleracea | B. oleracea/Ogura |
| B. o | B. oleracea | B. oleracea |

Moreover, the existence of a CMS character of good quality necessitates the presence of a DNA sequence which can be identified by DNA/DNA hybridisations on digestions. Thus, the present invention relates to a DNA sequence which it has been possible to define and which is characterised in that it contains a sequence which gives a 2.5-kb fragment after NcoI digestion, gives a 6.8-kb fragment after NruI digestion and gives a 4.4-kb fragment after SalI digestion.

This sequence can also be identified by hybridisations on the total RNA of male-sterile plants. A transcript of approximately 1,400 base pairs is demonstrated. It is absent from plants returning to fertility.

The definition of "undesirable" nucleotide sequences and of nucleotide sequences "essential" to an Ogura sterility according to the invention enables a plant material carrying chloroplasts which are compatible with the nuclear genome and carrying mitochondria of good quality to be selected, by DNA hybridisation techniques well known to those skilled in the art, without waiting to have an adult plant and the appearance of flowers and fruits. A highly efficacious tool for selecting plants possessing a male-sterile cytoplasm having good agronomic characteristics is hence at the user's disposal.

According to another aspect, the invention relates to a mitochondrion, characterised in that it contains a nucleotide sequence corresponding to a DNA exhibiting an at least 50% homology with the sequence bounded by the bases numbered 928 and 2273 in FIG. 1 (SEQ ID NO: 1) and coding for Ogura cytoplasmic male sterility; or alternatively the mitochondrion contains a DNA sequence carried by the sequence bounded by nucleotides 928 and 1569 in FIG. 1 (SEQ ID NO: 1) or possessing a 50% homology with this sequence, and which is transcribed to RNA in the mitochondria of male-sterile plants. This DNA can possess, in addition, the characteristics defined above, in particular the absence of undesirable sequences.

The present invention also relates to a Cruciferae cytoplasm, characterised in that it contains an "Ogura sterility" DNA sequence; this cytoplasm contains, in addition, chloroplasts of the same species or of another species but which are compatible with the nuclear genome.

The Ogura sterility sequence is characterised in that:
a) it is carried by the 2428-base pair DNA sequence (SEQ ID NO: 1) shown in FIG. 1,
b) it is bounded by nucleotides 928 and 2273 in FIG. 1 and corresponds to a transcript indicated by the broken line in FIG. 2 and visualised by molecular hybridisation (1.4) in FIG. 6,
c) it possesses an at least 50% homology with the said sequence mentioned in b), and confers, when it is present in the mitochondrial genome of a plant, a cytoplasmic male sterility on the said plant, or
d) it is carried by the sequence (SEQ ID NO: 1) bounded by nucleotides 928 and 1569 in FIG. 1 and is transcribed to RNA in the mitochondria of sterile plants, or
e) it possesses an at least 50% homology with the sequence described in d) and is transcribed to RNA in the mitochondria of sterile plants.

The present invention also relates to a plant of the Cruciferae family, characterised in that it contains chloroplasts and a nucleus of the same species or which are compatible, and mitochondria carrying a genome conferring the CMS character as defined above.

More specifically the present invention also relates to a plant belonging to the genus Brassica, characterised in that it contains chloroplasts and a nucleus of Brassica, and mitochondria carrying a genome conferring the CMS character as has been defined above.

This mitochondrial genome must also carry a number of genes of the Brassica species in question. This is achieved by recombination between the Ogura genome and the Brassica genome.

In particular, the present invention relates to a plant belonging to the species Brassica napus, characterised in that it contains a Brassica nucleus and in that the cytoplasm contains Brassica chloroplasts and male-sterile mitochondria carrying a DNA according to the present invention as has been defined above; these mitochondria can also carry the majority of the mitochondrial genes of Brassica napus (18S, Atp9, Atp6, CoxII, ndh1, cob). Brassica napus corresponds to colza or canola and swede.

The present invention relates to a plant of the species Brassica oleracea, characterised in that it contains a Brassica nucleus and in that the cytoplasm contains Brassica chloroplasts and mitochondria containing a DNA sequence coding for the CMS character as has been defined.

Brassica oleracea covers the various types of cabbage: headed cabbage, Brussels sprouts, kohl-rabi, broccoli, fodder kale and cauliflower.

The present invention also relates to a plant of the species Brassica campestris, characterised in that it contains a Brassica nucleus and in that the cytoplasm contains Brassica chloroplasts which are compatible with the nuclear genome and mitochondria containing a DNA sequence coding for the CMS character as has been defined.

Brassica campestris corresponds to rape, turnip and Chinese, Peking and Japanese cabbage.

Similarly, the present invention relates to a plant chosen from the group comprising B. juncea, B. nigra, B. hirta and B. carinata, characterised in that it contains a Brassica nucleus and in that the cytoplasm contains Brassica chloroplasts which are compatible with the nuclear genome and mitochondria containing a DNA sequence coding for the CMS character as has been defined.

According to another of its aspects, the subject of the present invention is a plant belonging to the genus Brassica and whose nuclear genome contains an Ogura sterility sequence as defined above as well as elements effecting its expression and the transport of the translation product into the mitochondrion. This plant can, in particular, belong to one of the following species: B. napus, B. oleracea, B. campestris, B. nigra, B. juncea, B. hirta and B. carinata.

The presence of the "Ogura sterility sequence" is necessary and sufficient for inducing a total absence of pollen in the absence of restorer genes. The pollination of these plants is effected normally as a result of a good production of nectar.

The morphology of the female organs is normal, and the fruits (siliques) formed contain a normal number of seeds. FIG. 5 shows the morphology observed in a normal control plant (z), a plant having aberrant morphology possessing the whole Ogura genome (z(6)) and Brassica oleracea chloroplasts, a cabbage plant carrying Brassica napus chloroplasts and male-sterile mitochondria having Brassica napus genes (z(A)), and plants carrying Brassica oleracea chloroplasts and recombinant mitochondria no longer containing the undesirable sequences (z(9) and z(17)). The plants have the following characteristics:

| GENOTYPE | CHLOROPLASTS | MITOCHONDRIA |
| --- | --- | --- |
| z | B. oleracea | B. oleracea |
| z (A) | B. napus | B. napus/Ogura |
| z (6) | B. oleracea | Ogura |
| z (9) | B. oleracea | B. oleracea/Ogura |
| z (17) | B. oleracea | B. oleracea/Ogura |

The genotypes z(A) and z(6) do not possess a suitable cytoplasmic male sterility system.

Such plants may be obtained, for example, by the protoplast fusion technique or by all other techniques which effect good recombination between the mitochondrial genome of the species in question and the Ogura mitochondrial genome. In such plants, fertility is restored by a single restorer gene, referred to as Rf1, originating from radish, which is not the case with plants which carry the whole of the unsuitable mitochondrial genome.

Such plants may also be obtained by natural or artificial sexual reproduction.

Plants possessing a mitochondrial genome according to the invention may also be obtained by gene transfer in the mitochondrion.

In all cases, these plants possess a suitable CMS system, namely:

a total male sterility, a morphology permitting good pollination and good seed production as illustrated in Table 1 and Table 2.

Thus, the present invention also relates to a method for preparing hybrid plants, characterised in that a plant possessing a suitable CMS character, containing the Ogura sterility sequence in its mitochondrial or nuclear genome, is crossed with a normal plant in the case of an edible or fodder crop, or with a plant providing a gene restoring fertility, Rf1, in the case where seeds are to be harvested. It also relates to a hybrid plant obtained by this method.

Generally speaking, the best agronomic characteristics are obtained with male-sterile plants possessing chloroplasts of the same species as the nucleus and mitochondria possessing a suitable male sterility system.

Table 1 shows the productivity of a cabbage line with different cytoplasms (the genotypes Z9 or Z17 are suitable). Table 2 shows the productivity of colza line with different cytoplasms (the genotypes Fu 27, Fu 58 and Fu 85 are suitable).

TABLE 1

PRODUCTIVITY OF THE z LINE
(SAUERKRAUT CABBAGE) WITH DIFFERENT CYTOPLASMS

| Cytoplasm | | | Seed harvest |
|---|---|---|---|
| Chloroplasts | Mitochondria | Genotypes | Grams/plant |
| B. oleracea | B. oleracea (fertile control) | (z) | 53.1 |
| B. napus | Ogura | (zC) | 0 |
| B. napus | Ogura/napus | (zA) | 22.7 |
| B. oleracea | Ogura | (z6) | 9.3 |
| Ogura | Ogura | (z0) | 20.1 |
| B. oleracea | Ogura/oleracea | (z9 or z17) | 91.8 |

The subject of the present invention is also a probe containing a sequence of at least 10 bases, and preferably 15 bases, of a sequence bounded by the nucleotides numbered 928 and 1569 in FIG. 1; the said probe can be labelled, for example by means of a radioactive base, or by any other means such as, for example, by fluorescence. This probe may be used for the demonstration of male sterility, and may be used, in particular, in the selection of clones.

Some characteristics and advantages of the present invention will be more clearly demonstrated in the examples which follow.

EXAMPLE 1

DEMONSTRATION OF THE DNA SEQUENCE RESPONSIBLE FOR OGURA CYTOPLASMIC MALE STERILITY

1. Plant

"Cybrid" denotes forms obtained by the fusion of isolated protoplasts followed by regeneration of the whole plant. This method of production enables cytoplasmic information originating from both parents to be mixed in the cell. Cybrid No. 13 was obtained from among 820 plants regenerated by protoplast fusions between an Ogura-cms, triazine-resistant B. napus cybrid (progeny of cybrid 77 described in Pelletier et al., 1983 and Chétrit et al., 1985) and the triazine-sensitive and fertile variety of Brutor origin. A triazine resistance test (Ducruet and Gasquez, 1978) carried out on a leaf sample of each regenerant enabled the type of chloroplast (triazine-resistant chloroplasts originating from the parent 77 or triazine-sensitive chloroplasts originating from the Brutor line) to be determined. The plants were cultivated and the flowering stage was observed. Plants exhibiting non-parental combinations (either sensitive/male-sterile or resistant/male-fertile) were selected as cybrids. Cybrid No. 13 was of the sensitive/male-sterile type. Cybrid 1 was of the resistant/male-fertile type.

TABLE 2

PRODUCTIVITY OF THE DARMOR LINE (WINTER COLZA)
WITH DIFFERENT CYTOPLASMS
* Yield
* Male-fertile and male-sterile (FU) DARMOR winter colza

| | Yield (% DARMOR) | Chloroplasts | Mitochondria |
|---|---|---|---|
| DARMOR | 100 (35 qx) | B. napus | B. napus |
| Fu 27 | 118 | B. napus | B. napus/Ogura |
| Fu 58 | 120 | B. napus | B. napus/Ogura |
| Fu 77 | 96 | B. campestris | Ogura |
| Fu 85 | 114 | B. napus | B. napus/Ogura |
| Fu 118 | 103 | B. napus | B. napus/Ogura |
| BIENVENUE | 108 | | |
| JET NEUF | 89 | | |

| | Components of the yield (Clermont-Ferrand) | | | | | | | | |
|---|---|---|---|---|---|---|---|---|---|
| | NSq | W1Sq | NSdPSq | NSd | W1Sd | TDM | HI | YLD | HT |
| DARMOR | 7183 | 81.9 | 9.9 | 70028 | 4.31 | 1077 | 0.256 | 31.6 | 120 |
| BIENVENU | 7334 | 80.7 | 11.2 | 81841 | 3.88 | 1064 | 0.269 | 30.7 | 109 |
| JET NEUF | 7977 | 87.7 | 8.6 | 67291 | 4.98 | 1176 | 0.262 | 33.3 | 115 |
| Fu 27 DARMOR | 9292 | 82.8 | 11.6 | 106188 | 4.09 | 1337 | 0.293 | 42.2 | 122 |
| Fu 58 DARMOR | 8617 | 76.5 | 11.7 | 99947 | 3.65 | 1228 | 0.270 | 36.0 | 131 |
| Fu 118 DARMOR* | 8389 | 84.6 | 11.0 | 92428 | 4.11 | 1243 | 0.276 | 38.1 | 132 |

NSq: Number of siliques/m$^2$ - W1Sq: Weight of one silique (mg) - NSdPSq: Number of seeds/silique
NSd: Number of seeds/m$^2$ - W1Sd: weight of one seed (mg) - TDM: Total dry matter (g/m$^2$)
HI: Harvest index (%) - YLD: Yield (qx/ha) - HT: Height (cm)
*These plants often possess deformed fruits (siliques).

2. Nucleic acid isolation

The total DNA was isolated from leaves originating from 4-week-old plants according to the method described by Dellaporta (1983). The mitochondrial DNA was extracted from leaves of 8-week-old plants as has been described by Vedel and Mathieu, 1982, with the following variants:

the mitochondria were not purified on a sucrose gradient before lysis, and lysis was carried out in 4% sarcosyl with 0.5 mg/ml proteinase K (Boehringer Mannheim GmbH) in 50 mM Tris pH 8, 20 mM EDTA. After precipitation, the mitochondrial DNA was purified by centrifugation on an ethidium bromide/caesium chloride gradient (method 1—Vedel and Mathieu, 1982) in polyallomer centrifuge tubes.

The total RNA was isolated from leaves or floral buds according to Logemann et al., 1987.

The mitochondrial RNA was extracted from 8-week-old cauliflowers according to the technique of Stern and Newton, 1986.

3. Restriction analyses of the mitochondrial DNA and agarose gel electrophoresis These were carried out as described in Pelletier et al., 1983. The total or mitochondrial RNA was loaded onto electrophoresis gels containing formaldehyde, as has been described by Sambrook et al., 1989.

4. Hybridisation

Transfer of DNA or RNA onto nylon filters (Hybond-N, Amersham) was carried out by capillary absorption with 6×SSC or 10×SSPE, respectively, according to the manufacturer's instructions. Prehybridisation and hybridisation were performed according to Amersham, using probes labelled by the multiprimer DNA labelling system (Amersham) after purification on Sephadex G-50 columns (Sambrook et al., 1989).

5. Cloning of the mitochondrial DNA

Two genomic libraries of male-sterile (13-7) and revertant (13-6) cybrid lines were constructed in a phage lambda EMBL3 vector cultured on the restrictive E. coli strain Nm539 (Frischauf et al., 1983). Approximately $2.5 \times 10^4$ clones per µg of mitochondrial DNA were obtained.

The mitochondrial DNA libraries were assayed and plated out in order to isolate the plaques, which were transferred onto nylon filters as described in Sambrook et al., 1989. The hybridisation probe used to screen the two libraries of mitochondrial DNA was prepared as follows: the mitochondrial DNA fragment specific for the cms was eluted using the Gene cleans procedure (BIO 101 INC.) from a mitochondrial DNA digestion product loaded onto a preparative agarose gel. The eluted DNA was then labelled as has been described.

The extraction of lambda DNA, subcloning of the 2.5 NcoI fragment into the NcoI site of pTrc99A (Amann et al., 1988) and extractions of plasmid DNA were performed according to the protocols of Sambrook et al., 1989. The recombinant plasmids were introduced into an E. coli strain NM522 (Gough and Murray, 1983).

6. Genetic study of cybrid 13 and its progeny

In the first generation of progeny obtained by pollination of cybrid 13 with Brutor, composed of 13 plants, 5 are totally male-sterile (including plants 13-2 and 13-7), one is male-fertile (No. 13-6) and 7 are almost completely sterile with a few male-fertile flowers.

The fertile plant 13-6 was self-pollinated and crossed with Brutor. In both cases, only fertile plants (43 and 42, respectively) are obtained.

In the crosses between the male-sterile plant No. 13-7 and Brutor, 24 progeny are completely sterile and 6 possess a few fertile flowers, a similar result to that observed with the cybrid itself. The plant 13-2 was crossed with the restorer line RF, which is heterozygotic for the specific restorer genes for Ogura male sterility (Chétrit et al., 1985). The progeny of this cross is composed of 53 male-sterile plants, 37 male-fertile plants and 9 plants which are almost completely sterile although they possess a few fertile flowers. These results suggest that the male-sterile plants of the cybrid family 13 contain the Ogura-cms determinant, like the other cybrids studied beforehand with a simpler restoration profile (Chétrit et al., 1985).

At this stage of the study, two possibilities may be envisaged: either cybrid 13 contains a mixture of "male-fertile" and "male-sterile" mitochondrial genomes, and it is possible to select further for both phenotypes, or cybrid 13 contains a recombinant mitochondrial genome of unstable structure which reverts to a more stable "fertile" configuration, and it will be impossible to maintain a homogeneous male-sterile phenotype among subsequent generations.

Male-sterile plants obtained from the progeny of the male-sterile plant No. 13-7 were developed both by taking cuttings and by sexual crossing with Brutor. After a variable number of generations (1 to 5) by both methods, all the families give fertile plants. In contrast, the completely fertile plants thereby obtained never give rise again to sterile plants.

In the light of these results, it may be considered that the second explanation proposed above, that is to say that cybrid 13 carries an unstable mitochondrial genome which loses the Ogura-cms determinant during the process leading to a "fertile" configuration, without the possibility of a return to a sterile phenotype, is the correct one.

7. Comparison between the mitochondrial DNAs of male-sterile and fertile revertant offspring. Isolation of a fragment specific to the male-sterile plants The mitochondrial DNA was extracted from the leaves of male-sterile 13-7 progeny and of fertile revertants (13-6 or 13-7 progeny), and digested with several restriction enzymes in order to compare their restriction profiles. The mitochondrial genomes of the two types are very similar, since no difference can be observed between the restriction profile of the male-sterile mitochondria and fertile revertants using various enzymes. However, a 6.8-kb restriction fragment was detected in the restriction profile of the mitochondrial DNA of the male-sterile plants digested with NruI, and was never observed in the corresponding profiles of the fertile revertants.

The fragment (referred to as N6.8) was eluted from an agarose gel, labelled and used as a probe on NruI mitochondrial DNA restriction profiles: a large signal at 6.8 kb was observed in all the male-sterile progeny of cybrid 13, whereas no fragment of this size hybridised with the probe in the genomes of mitochondria of fertile revertants. In addition, the probe N6.8 hybridises with a 6.8-kb fragment in the Ogura mitochondrial DNA digested with NruI, but not in B. napus cv Brutor, showing the Ogura origin of this fragment.

A lambda library containing mitochondrial DNA extracts originating from male-sterile plants (13-7) was tested with the eluted labelled fragment, and out of 8 clones hybridising, 2 recombinant phages were isolated, containing the whole N6.8 fragment and adjacent sequences. A detailed restriction map of this region was obtained. Hybridisation of the restriction profiles of the mitochondrial DNA originating from fertile and sterile progeny of cybrid 13 with N6.8 as a probe enabled the region specific for the male-sterile genotype to be limited to a 2.5-kb NcoI fragment.

The 2.5-kb NcoI fragment was labelled and used as a probe with respect to mitochondrial DNA originating from 13-7 and 13-6 progeny digested with NcoI. Apart from the signal at 2.5 kb which is specific for the male-sterile profile, several NcoI fragments hybridise in both the fertile revertant and male-sterile profiles; these fragments are at 2.2, 10 and 14 kb. A 2.7-kb NcoI fragment hybridises strongly in the mitochondrial genome of the fertile progeny and not in that of the sterile progeny. Analysis of this hybridisation profile leads to the conclusion that the 2.5-kb NcoI fragment, although specific for the male-sterile mitochondrial DNA, contains sequences which are repeated elsewhere in the mitochondrial genome (on 2.2-, 10- and 14-kb fragments after NcoI), and these repeated sequences are also present in the mitochondrial DNA of fertile revertants apart from the specific 2.7-kb fragment.

The total RNA is extracted from leaves or buds of progeny of cybrids 13, or of male-sterile or fertile cybrids (originating from other fusion experiments) and of Brutor line. Northern blotting was carried out and the blots were hybridised with a probe corresponding to the insert of the lambda clone containing N6.8 described in Example 3. A major 1.4-kb transcript was detected in all the male-sterile cybrids, including cybrid 13-7, whereas no transcript of this size was observed in the Brutor line, or in the two fertile cybrids (different from 13). Moreover, fertile plants possess a 1.1-kb transcript which hybridises with the probe, which is absent or present at a very low level in all the male-sterile cybrids tested. Several transcripts common to all the samples hybridise weakly with the probe on account of the large size of the labelled insert. It was confirmed that the mitochondrial transcripts can be detected in samples of total RNA by hybridisation of the same Northern blot with a DNA fragment containing the atpa gene sequence.

The same specific 1.4 transcript was found in the Ogura mitochondrial RNA extracted from cauliflowers, using the 2.5 NcoI fragment as a probe. The exact limits of this transcript were determined using subclones of the 2.5 NcoI fragment as a probe 8. Study of cybrid 1 and its progeny Cybrid 1 was male-fertile. In its progeny, the plant 1.12 was fertile and the plant 1.18 sterile. The plant 1.12 gave in its progeny sterile plants ($S_3$) and fertile plants ($RF_3$). The plant 1.18 gave sterile plants ($S_2$) and a fertile branch ($RF_2$). The plants $S_2$ and $S_3$ are restored by the same nuclear gene that restores pollen fertility as the sterile cybrid 13.

On hybridisation with the labelled 2.5-kb NcoI fragment, the mitochondrial DNA of the plants $S_2$ and $S_3$ does not give a signal at 2.5 kb on NcoI digestion, or a signal at 6.8 kb on NruI digestion.

Similarly, hybridisation with the total RNA (Northern blotting) with a probe corresponding to the ORFB sequence does not give a signal at 1.4 kb as occurs with the sterile cybrid 13. In contrast, a probe corresponding to the sequence bounded by nucleotides 928 and 1569 in FIG. 1 (SEQ ID NO: 1) gives a signal in Northern blotting at approximately 1.3 kb. This signal is absent from the RNA of the plants $RF_1$, $RF_2$, $RF_3$ or Brutor. Similarly, it is possible to use this sequence (928–1569) as a probe in dot-blotting of total RNA, and in this case, only the male-sterile plants, and all of them, give a signal.

These results indicate that the $S_2$ and $S_3$ plants, although male-sterile, have not retained the nucleotide sequence (SEQ ID NO: 1) described in FIG. 1 in its original conformation, and demonstrate that, in this sequence, the portion bounded by nucleotides 928 and 1569 is that which carries the "Ogura sterility" specific determinant, which makes the plants male-sterile when this sequence is transcribed.

This sequence has no significant homology with the sequences present in the data banks.

EXAMPLE 2

DEMONSTRATION OF UNDESIRABLE SEQUENCES IN THE OGURA MITOCHONDRIAL GENOME

A collection of cybrids was obtained in the species *B. napus* by protoplast fusion between a colza carrying Ogura cytoplasm and a normal colza. The former is male-sterile and chlorophyll-deficient at low temperature, while the latter is normally green and fertile. The cybrids were sorted from among the regenerated plants and those which were male-sterile and normally green were adopted.

In the same manner, a collection of cybrids was obtained in the species *B. oleracea* by protoplast fusion between a cabbage carrying Ogura cytoplasm and a normal cabbage. The cybrids which were male-sterile and normally green were adopted from among the regenerated plants.

These cybrids were crossed with different varieties, of colza in the first case and cabbage in the second. The crosses were repeated at each generation with the same varieties so as to obtain a defined genotype close to that of the recurring variety.

These different varieties, thereby converted with the cytoplasms of different cybrids, were subjected to agronomic tests to measure seed production, which depends on several factors: a sufficient production of nectar to effect pollination by insects, and a normal floral morphology in order that this pollination is effective and the fruits develop normally.

The collection of cybrids could thus be divided into two batches:
- a batch of cybrids possessing a male sterility suited to commercial seed production,
- a batch of cybrids not possessing all the characteristics favourable to a good commercial seed production.

The colza cybrids Nos. 27, 58 and 85 and the cabbage cybrids Nos. 9, 17, 21, 24 and 27c, for example, belong to the first batch.

The colza cybrids Nos. 23s, 77 and 118 and the cabbage cybrids Nos. 1, 6 and 14, for example, belong to the second batch.

The total DNA of these cybrids was subjected to enzymatic digestions with SalI, NcoI, NruI, BglI, PstI and KpnI. The Southern blots obtained were hybridised with various mitochondrial probes Atpa, Cob, Cox1, Atp6, 26S and 18S and two fragments of Ogura genome, of 2.5 kb derived from an NcoI digestion and of 19.4 kb derived from an NruI digestion.

The two batches of cybrids differ in that:
a) Nos. 23s, 77 and 11s in colza and 1, 16 and 11 in cabbage do possess the region of the Ogura genome which surrounds the Cox1 gene, recognisable by 10.7-kb BglI or 11-kb NruI fragments, and the region of the Ogura genome which surrounds one of the formylmethionine transfer RNA genes, recognisable by 5.1-kb SalI or 15-kb NruI fragments.
b) Nos. 27, 58 and 85 in colza and 9, 17, 21, 24 and 27c in cabbage do not possess the corresponding regions, which have been replaced, as a result of recombinations between the genomes of the two parents which have been fused, by analogous regions of the mitochondrial genome of colza in Nos. 27, 58 and 85 and of cabbage in Nos. 9, 17, 21, 24 and 27c.

It is deduced from this that the two regions in question of the Ogura genome are undesirable if it is desired to have a male sterility system suited to commercial seed production.

EXAMPLE 3

This example illustrates the value of knowing the "Ogura male sterility" sequences and the undesirable sequences for performing an immediate sorting of the cybrids obtained without having to wait several years for back-crossing and agronomic tests.

Protoplasts of a Brassica plant carrying the Ogura cytoplasm are fused with protoplasts of the Brassica species in question. The colonies derived from fusion are cultured in vitro and set up to regenerate on a medium which promotes bud formation (see Pelletier et al., 1983).

From one gram of fresh material, either a callus or a fragment of the regenerated plantlet, it is possible by the techniques described above to isolate the total DNA. After SalI digestion, Southern type hybridisation with the probe bounded by nucleotides Nos. 389 and 1199 (see FIG. 1) should give a signal only for a size of 4.4 kb (should not give a signal at 5.1 kb). Similarly, after NruI digestion and hybridisation with a probe carrying the Cox1 gene, a signal should be obtained for a size different from 11 kb.

These hybridisations enable it to be predicted that the plant which has been obtained will indeed be male-sterile and suited to commercial seed production.

EXAMPLE 4

This example is a variant of Example 3, based on the idea of carrying out sexual crossing between the two parents under special conditions or with particular genotypes instead of carrying out protoplast fusions, with the result that, in contrast to the known processes of fertilisation in plants, there is mixing of the cytoplasms of the oosphere and of the pollen tube or the male gamete. If such methods were described, an early sorting could be performed in the same manner on young plants derived from these artificial fertilisations, using the same probes and the same criteria as in Example 3.

EXAMPLE 5

This example illustrates the value of knowing the Ogura sterility sequence in a type of genetic manipulation which has already been described in yeast (Johnston et al., 1988).

Starting with a normal Brassica plant, meristems or alternatively cells in vitro are bombarded with micro-particles coated with DNA carrying the Ogura sterility sequence. The plants obtained in the progeny of the treated meristems or the regenerated plantlets will be cytoplasmic male-sterile if the DNA has been able to enter the mitochondria and become integrated in the genome of these organelles. This procedure will avoid the problems that are created by the undesirable sequences when Ogura radish chloroplasts or the sequences so defined of the Ogura mitochondrial genome are involved.

EXAMPLE 6

This example illustrates the value of knowing the "Ogura sterility" sequence in the construction by genetic engineering of a nuclear, instead of a cytoplasmic, male sterility conforming to Mendelian inheritance.

Starting with the mitochondrial DNA sequence bounded by nucleotides 928 and 1569 (SEQ ID NO: 1), a chimeric gene may be constructed which will be transcribed, after genetic transformation of Brassica cells or cells of another genus, in the nucleus of the cells of the transformed plants obtained. If the chimeric gene contains a pre-sequence which enables its protein translation product to be imported into the mitochondrion, these transformants will be male-sterile and this character will behave as a dominant Mendelian character.

REFERENCES

Amann E., Ochs B. and Abel K.-J. (1988) Gene 69:301–315

Bannerot H., Boulidard L., Cauderon Y. and Tempé J. (1974) Proc Eucarpia Meeting Cruciferae 25:52–54

Bannerot H., Boulidard L. and Chupeau Y. (1977) Eucarpia Cruciferae Newsl: 2–16

Chétrit P., Mathieu C., Vedel F., Pelletier G. and Primard C. (1985) Theor Appl Genet 69:361–366

Dellaporta S. L., Wood J. and Hicks J. B. (1983) Plant Mol Biol Rep 1:19–21

Ducruet J. M. and Gasquez J. (1978) Chemosphere 8:691–696

Frishauf A. M., Lehrach H., Poutska A. and Murray N. (1983) J Mol Biol 170:827–842

Gough J. and Murray N. (1983) J Mol Biol 166:1–19

Hiesel R., Shobel W., Schuster W. and Brennicke A. (1987) EMBO J 6:29–34

Johnston S. A., Anziano P. Q., Shark K., Sanford J. C. and Butow R. A. (1988) Science 240:1538–1541

Logemann J., Schell J. and Willmitzer L. (1987) Analytical Biochem 163:16–20

Ogura H. (1968) Mem Fac Agric Kagoshima Univ 6:39–78

Pelletier G., Primard C., Vedel F., Chétrit P., Rémy R., Rousselle P. and Renard M. (1983) Mol Gen Genet 191:244–250

Sambrook J., Fritsch E. F. and Maniatis T. (1989) Molecular cloning, Cold Spring Harbor Laboratory, Cold Spring Harbor, N.Y.

Stern D. B. and Newton K. J. (1986) Methods Enzymol 118:488–496

Vedel F. and Mathieu C. (1982) Anal Biochem 127:1–8

---

We claim:

1. A recombinant plant nuclear or mitochondrial genome, which comprises:
   a) a DNA sequence bounded by the nucleotides numbered 928 and 1569 in FIG. 1 (SEQ ID NO: 1), or
   b) a DNA sequence encoding a protein translation product identical to that encoded by a)

wherein said sequence confers cytoplasmic male sterility on a plant when it is present in the mitochondrial genome of said plant, said recombinant genome being devoid of a functional copy of a gene of an Ogura genome, said gene being identified as i) a formylmethionine transfer RNA gene used for translation initiation, said formylmethionine transfer RNA gene being characterized by yielding a DNA fragment of 15 kb after NruI digestion or of 5.1 kb after SalI digestion, said DNA fragment revealed by hybridization with a probe corresponding to the sequence bounded by bases 389 and 1199 of the sequence shown in FIG. 1 (SEQ ID NO: 1); or ii) a Cox1 gene coding for subunit No. 1 of cytochrome oxidase, said Cox1 gene being characterized by yielding a DNA fragment of 10.7 kb after BglI digestion or of 11 kb after NruI digestion, said DNA fragment being revealed by hybridization with a Cox1 probe.

2. The nuclear or mitochondrial genome according to claim 1, wherein said genome contains a sequence which gives a 2.5-kb fragment after NcoI digestion, gives a 6.8-kb fragment after NruI digestion and a 4.4-kb fragment after SalI digestion.

3. The nuclear genome of claim 1, wherein said genome further comprises a presequence enabling the translation product of said sequence to be imported into a mitochondrion.

4. The genome according to claim 1, wherein said genome is mitochondrial.

5. A mitochondrion comprising the genome according to claim 4.

6. Cytoplasm, comprising the mitochondrial genome according to claim 4, and further comprising chloroplasts of the same species as said nuclear genome or of another species compatible with said nuclear genome.

7. A plant belonging to the genus Brassica, comprising Brassica chloroplasts which are compatible with said nuclear genome of said plant and mitochondria according to claim 5.

8. A plant belonging to the genus Brassica having a nuclear genome comprising the genome according to claim 3 and elements affecting its expression and the transport of its translation product into the mitochondrion.

9. The plant according to claim 7, wherein said plant belongs to the species *Brassica napus*.

10. The plant according to claim 7, wherein said plant belongs to the species *Brassica oleracea*.

11. The plant according to claim 7, wherein said plant belongs to the species *Brassica campestris*.

12. The plant according to claim 7, wherein said plant belongs to the species *Brassica juncea*.

13. The plant according to claim 7, wherein said plant belongs to the species *Brassica nigra*.

14. The plant according to claim 7, wherein said plant belongs to the species *Brassica hirta*.

15. The plant according to claim 7, wherein said plant belongs to the species *Brassica carinata*.

16. The plant according to claim 7, wherein said plant belongs to the species *B. napus, B. oleracea, B. campestris, B. nigra, B. juncea, B. hirta* or *B. carinata*.

17. The plant according to claim 7, wherein said plant is obtained by protoplast fusion.

18. The plant according to claim 7, wherein said plant is obtained by sexual reproduction.

19. The plant according to claim 7, wherein said plant is obtained by gene transfer in the mitochondrion.

20. A method for preparing hybrid plants, comprising crossing a plant possessing the male-sterile cytoplasmic character according to claim 6 with a plant of the same species.

21. A nucleic acid probe comprising a first sequence of at least 15 bases of a second sequence bounded by the nucleotides numbered 928 and 1569 shown in FIG. 1 (SEQ ID NO: 1), said second sequence conferring cytoplasmic male sterility character, labelled by a radioactive or non-radioactive means.

22. An isolated DNA molecule, which comprises:
   a) a DNA sequence bounded by the nucleotides numbered 928 and 1569 in FIG. 1 (SEQ ID NO: 1), or
   b) a DNA sequence encoding a protein translation product identical to that encoded by a);

wherein said sequence confers cytoplasmic male sterility on a plant when it is present in the mitochondrial genome of said plant and is transcribed to RNA in the mitochondria of said plant.

23. The DNA molecule according to claim 22, which comprises the sequence bounded by the nucleotides numbered 928 and 1569 in FIG. 1 (SEQ ID NO: 1).

24. The DNA molecule according to claim 22, which comprises the sequence bounded by nucleotides 928 and 2273 in FIG. 1 (SEQ ID NO: 1) or a sequence encoding a protein translation product identical to said sequence bounded by nucleotides 928 and 2273; wherein said sequence is transcribed to RNA in the mitochondria of a male sterile plant.

25. The DNA molecule according to claim 24, which comprises the sequence bounded by the nucleotides numbered 928 and 2273 in FIG. 1 (SEQ ID NO: 1), wherein said sequence confers cytoplasmic male sterility on a plant when it is present in the mitochondrial genome of said plant.

26. The hybrid plant obtained by the method according to claim 20.

27. A method for preparing hybrid plants, comprising crossing a plant possessing the male-sterile cytoplasmic character according to claim 6 with a plant of the same species, possessing a gene restoring fertility, Rf1.

28. The hybrid plant obtained by the method of claim 27.

* * * * *